(12) United States Patent
Ota et al.

(10) Patent No.: US 10,953,131 B2
(45) Date of Patent: Mar. 23, 2021

(54) METHOD FOR PRODUCING CALCIUM PHOSPHATE MOLDED ARTICLE, CALCIUM PHOSPHATE MOLDED ARTICLE, AND MATERIAL FOR TRANSPLANTATION

(71) Applicant: FUJIFILM Corporation, Tokyo (JP)

(72) Inventors: Hiroshi Ota, Ashigarakami-gun (JP); Manabu Katsumura, Ashigarakami-gun (JP); Kazuya Kawasaki, Ashigarakami-gun (JP); Yoshio Ishii, Ashigarakami-gun (JP); Hideo Fushimi, Ashigarakami-gun (JP); Takahiro Hiratsuka, Ashigarakami-gun (JP); Ai Okamura, Ashigarakami-gun (JP); Mamoru Nishitani, Ashigarakami-gun (JP); Masayuki Ezumi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/204,987

(22) Filed: Nov. 29, 2018

(65) Prior Publication Data

US 2019/0167841 A1    Jun. 6, 2019

Related U.S. Application Data

(63) Continuation of application No. PCT/JP2017/020130, filed on May 30, 2017.

(30) Foreign Application Priority Data

May 30, 2016 (JP) .............................. JP2016-107615
Dec. 9, 2016 (JP) .............................. JP2016-239826

(51) Int. Cl.
*A61L 27/12* (2006.01)
*B28B 1/30* (2006.01)
(Continued)

(52) U.S. Cl.
CPC .............. *A61L 27/12* (2013.01); *A61L 27/222* (2013.01); *A61L 27/34* (2013.01); *A61L 27/427* (2013.01);
(Continued)

(58) Field of Classification Search
CPC ........ A61L 27/12; A61L 27/427; A61L 27/58; A61L 27/34; A61L 27/222;
(Continued)

(56) References Cited

U.S. PATENT DOCUMENTS 4,330,514 A * 5/1982 Nagai ..................... A61L 27/12
106/35
2005/0158399 A1    7/2005 Yu et al.
(Continued)

FOREIGN PATENT DOCUMENTS

CN      1460526 A      12/2003
CN      1644561 A      7/2005
(Continued)

OTHER PUBLICATIONS

Japanese Office Action, dated Nov. 12, 2019, for corresponding Japanese Application No. 2018-520931, with an English machine translation.
(Continued)

*Primary Examiner* — Carlos A Azpuru
(74) *Attorney, Agent, or Firm* — Birch, Stewart, Kolasch & Birch, LLP

(57) ABSTRACT

Provided are a method for rapidly producing a calcium phosphate molded article having high strength with high shaping precision, a calcium phosphate molded article produced by the method, and a material for transplantation. Disclosed is a method for producing a calcium phosphate molded article, the method including: step (a) of forming a layer containing a calcium phosphate powder having a ratio
(Continued)

of the numbers of atoms of Ca/P of 1.4 to 1.8 on a substrate; and step (b) of producing a calcium phosphate molded article by jetting an organic acid solution having a pH of 3.5 or lower and including an organic acid whose calcium salt has a solubility in water of 1 g/100 mL or less, through a nozzle unit into a liquid droplet state, thereby dropping the organic acid solution onto the layer containing a calcium phosphate powder formed in step (a).

9 Claims, 16 Drawing Sheets

Specification includes a Sequence Listing.

(51) Int. Cl.
    *A61L 27/34*     (2006.01)
    *C07K 14/78*     (2006.01)
    *C04B 35/447*     (2006.01)
    *A61L 27/58*     (2006.01)
    *A61L 27/42*     (2006.01)
    *B29C 67/00*     (2017.01)
    *A61L 27/22*     (2006.01)
    *B28B 1/00*     (2006.01)
    *B33Y 80/00*     (2015.01)

(52) U.S. Cl.
    CPC .............. *A61L 27/58* (2013.01); *B28B 1/001* (2013.01); *B28B 1/30* (2013.01); *B29C 67/00* (2013.01); *C04B 35/447* (2013.01); *C07K 14/78* (2013.01); *A61L 2430/02* (2013.01); *A61L 2430/04* (2013.01); *A61L 2430/06* (2013.01); *A61L 2430/38* (2013.01); *B33Y 80/00* (2014.12)

(58) Field of Classification Search
    CPC .............. A61L 2430/04; A61L 2430/38; A61L 2430/02; B29C 67/00; C04B 35/447; C07K 14/78; B28B 1/001; B28B 1/30; B33Y 80/00
    See application file for complete search history.

(56) References Cited

U.S. PATENT DOCUMENTS

| | | |
|---|---|---|
| 2006/0013894 A1 | 1/2006 | Yamamoto et al. |
| 2007/0128245 A1* | 6/2007 | Rosenberg .............. A61L 27/54 424/423 |
| 2007/0181239 A1 | 8/2007 | Yamazawa et al. |
| 2007/0231364 A1 | 10/2007 | Nishimoto et al. |
| 2009/0178531 A1 | 7/2009 | Fuchs et al. |
| 2011/0158963 A1 | 6/2011 | Font Pérez et al. |
| 2012/0165263 A1 | 6/2012 | Hiratsuka et al. |
| 2012/0210909 A1 | 8/2012 | Chu et al. |
| 2015/0259247 A1 | 9/2015 | Watanabe |
| 2017/0189960 A1 | 7/2017 | Ibe |

FOREIGN PATENT DOCUMENTS

| | | |
|---|---|---|
| CN | 101420922 A | 4/2009 |
| CN | 101745148 A | 6/2010 |
| CN | 102089238 A | 6/2011 |
| CN | 102625717 A | 8/2012 |
| CN | 104906631 A | 9/2015 |
| DE | 102006062000 A1 | 7/2006 |
| EP | 2781227 A1 | 9/2014 |
| EP | 2974752 A1 | 1/2016 |
| JP | 2001-95913 A | 4/2001 |
| JP | 2004-202126 A | 7/2004 |
| JP | 2006-25915 A | 2/2006 |
| JP | 2013-106721 A | 6/2013 |
| JP | 2013-202213 A | 10/2013 |
| JP | 2015-174792 A | 10/2015 |
| JP | 2015-187058 A | 10/2015 |
| JP | 2015174792 * | 10/2015 |
| WO | WO 02/083194 A1 | 10/2002 |
| WO | WO 2005/011536 A1 | 2/2005 |
| WO | WO 2005/105164 A1 | 11/2005 |
| WO | WO 2015/194678 A1 | 12/2015 |

OTHER PUBLICATIONS

Database WPI Week 201370, "Material useful for regenerating hard tissue used in regenerative medicine, comprises recombinant gelatin and calcium phosphate," Accession No. 2013-R07348, XP-002794057, Oct. 7, 2013, 2 pages.
Extended European Search Report for European Application No. 17806689.0, dated Sep. 16, 2019.
Furusawa et al., "Enhancement of mechanical strength and in vivo cytocompatibility of porous ß-tricalcium phosphate ceramics by gelatin coating," International Journal of Implant Dentistry, vol. 2, No. 4, 2016 (published online Feb. 6, 2016), pp. 1-6.
Kim et al., "Gelatin-layered and multi-sized porous ß-tricalcium phosphate for tissue engineering scaffold," Nanoscale Research Letters, vol. 7, No. 78, Jan. 17, 2012, pp. pp. 1-5.
Nguyen et al., "A Combination of Biphasic Calcium Phosphate Scaffold with Hyaluronic Acid—Gelatin Hydrogel as a New Tool for Bone Regeneration," Tissue Engineering: Part A, vol. 20, Nos. 13-14, 2014 (published online Mar. 19, 2014), 12 pages.
International Preliminary Report on Patentability and Written Opinion of the International Searching Authority (Forms PCT/IB/326, PCT/IB/373 and PCT/ISA/237) for International Application No. PCT/JP2017/020130, dated Dec. 13, 2018, with English translation.
International Search Report (Form PCT/ISA/210) for International Application No. PCT/JP2017/020130, dated Aug. 15, 2017, with English translation.
Nakahara, "Dictionary of Inorganic Compounds & Complexes," Kodansha Ltd., Jun. 1997, p. 163 (2 pages total).
Khalyfa et al., "Development of a new calcium phosphate powder-binder system for the 3D printing of patient specific implants," J Mater Sci: Mater Med, vol. 18, 2007 (published online Jan. 11, 2007), pp. 909-916.
Partial Supplementary European Search Report for European Application No. 17806689.0, dated May 13, 2019.
Korean Office Action for corresponding Korean Application No. 10-2018-7034917, dated Jun. 25, 2020, with an English translation.
Chinese Office Action and Search Report for corresponding Chinese Application No. 201780033977.5, dated Dec. 25, 2020, with partial English translation of the Office Action.

* cited by examiner

MIXED POWDER

TTCP POWDER

DCPD POWDER

| | WEEK 0 | WEEK 2 | WEEK 4 | WEEK 6 |
|---|---|---|---|---|
| LOWER HALF OF MOLDED ARTICLE B | | | | |
| CROSS-SECTION OF MOLDED ARTICLE B | | | | |

METHOD FOR PRODUCING CALCIUM PHOSPHATE MOLDED ARTICLE, CALCIUM PHOSPHATE MOLDED ARTICLE, AND MATERIAL FOR TRANSPLANTATION

CROSS-REFERENCE TO RELATED APPLICATIONS

This application is a Continuation of PCT International Application No. PCT/JP2017/020130 filed on May 30, 2017, which claims priority under 35 U.S.C § 119(a) to Japanese Patent Application No. 2016-107615 filed on May 30, 2016 and Japanese Patent Application No. 2016-239826 filed on Dec. 9, 2016. Each of the above application(s) is hereby expressly incorporated by reference, in its entirety, into the present application.

REFERENCE TO SEQUENCE LISTING SUBMITTED VIA EFS-WEB

This application includes an electronically submitted sequence listing in .txt format. The .txt file contains a sequence listing entitled "2019-02-05 2870-0708PUS1 ST25.txt" created on Feb. 5, 2019 and is 7,248 bytes in size. The sequence listing contained in this .txt file is part of the specification and is hereby incorporated by reference herein in its entirety.

BACKGROUND OF THE INVENTION

1. Field of the Invention

The present invention relates to a method for producing a calcium phosphate molded article by jetting an organic acid solution through a nozzle unit into a liquid droplet state, and thereby dropping the organic acid solution on a layer containing a calcium phosphate powder. The invention also relates to a calcium phosphate molded article. The invention also relates to a material for transplantation.

2. Description of the Related Art

Practicalization of regenerative medicine that promotes regeneration of biological tissues or organs with functional disorders or functional incompetence is currently underway. Regenerative medicine offers medical technologies of using cells, scaffolding, and one or more growth factors on a biological tissue that cannot be recovered only by the natural healing abilities possessed by a living body, and thereby regenerating the same morphology and functions as those of the original tissue. In regard to the regenerative medicine, there are occasions in which calcium phosphate molded articles are used.

JP2001-095913A describes a calcium phosphate cement and a calcium phosphate powder used for medical and dental purposes. In JP2001-095913A, specifically, a calcium phosphate cement formed by malaxating a powder of calcium phosphate and a liquid agent for hardening is described, the calcium phosphate cement having a consistency as defined in JIS T6602 of 2 to 100 mm in a case in which the powder liquid ratio between the powder and the liquid agent is changed in the range of 1.5 to 3.5. In WO2005/011536A, an artificial bone molding method is described, the method being based on a powder lamination method including: a) a powder layer forming step of forming a powdery bone material composed of an inorganic component such as calcium phosphate and other bone components into a planar powder layer; b) a partial hardening step of spraying a biocompatible aqueous solution to a portion of the powder layer and hardening the sprayed portion; c) an artificial bone molding step of repeating steps (a) and (b) to perform lamination and thereby molding an artificial bone having a desired three-dimensional structure where the hardened portions are connected. In JP2006-025915A, there is described a method for producing a calcium phosphate-based bone prosthetic material by producing a mixed liquid including a calcium solution and a phosphoric acid solution, incorporating a parent material formed from calcium phosphate into the mixed liquid during the production, thereby depositing calcium phosphate on the parent material, and heat-treating a complex thus obtained.

In JP2013-106721A, it is described that a member for tissue regeneration including a biodegradable resin film containing cytokines and calcium phosphate, the member for tissue regeneration having a gradient structure in which the ratio between cytokines and calcium phosphate continuously increases or decreases in the thickness direction, is formed by an inkjet method. Furthermore, JP2015-187058A describes a powdery material for additive fabrication comprising a calcium phosphate powder, in which an organic compound having a phosphoric acid group or a carboxyl group has been applied in a predetermined amount on the surface of the calcium phosphate powder, a powder formed from an organic compound having a phosphoric acid group or a carboxyl group is included in a predetermined amount, and the hydroxyapatite (HAp) conversion ratio of a hardened product obtained by hardening the powdery material for additive fabrication is 1% or less.

SUMMARY OF THE INVENTION

As described above, it is known to use a material including calcium phosphate as a bone prosthetic material or a member for tissue regeneration; however, development of a method for rapidly producing a calcium phosphate molded article having high strength with high shaping precision has been desired.

It is an object of the present invention to provide a method for rapidly producing a calcium phosphate molded article having high strength with high shaping precision, a calcium phosphate molded article, and a material for transplantation.

The inventors of the present invention conducted a thorough investigation in order to solve the problems described above, and as a result, the inventors found that a calcium phosphate molded article having high strength can be rapidly produced with high shaping precision, by forming a layer containing a calcium phosphate powder having a ratio of the numbers of atoms of Ca/P (calcium/phosphorus) of 1.4 to 1.8 on a substrate; subsequently jetting an organic acid solution having a pH of 3.5 or lower and including an organic acid whose calcium salt has a solubility in water of 1 g/100 mL or less, through a nozzle unit into a liquid droplet state; and thereby dropping the organic acid solution onto the layer containing the calcium phosphate powder. This invention was completed based on these findings.

That is, according to the invention, the following inventions are provided.

<1> A method for producing a calcium phosphate molded article, the method comprising:

step (a) of forming a layer containing a calcium phosphate powder having a ratio of the numbers of atoms of Ca/P of 1.4 to 1.8 on a substrate; and step (b) of producing a calcium phosphate molded article by jetting an organic acid solution having a pH of 3.5 or lower and including an organic acid whose calcium salt has a solubility in water of 1 g/100 mL or less, through a nozzle unit into a liquid droplet state, thereby dropping the organic acid solution onto the layer containing a calcium phosphate powder formed in step (a).

<2> The method for producing a calcium phosphate molded article according to <1>, wherein the organic acid used in step (b) is at least one selected from the group consisting of citric acid, oxalic acid, tartaric acid, malonic acid, and malic acid.

<3> The method for producing a calcium phosphate molded article according to <1> or <2>, further comprising, after the above-described step (b):

step (c) of forming a layer containing a calcium phosphate powder having a ratio of the numbers of atoms of Ca/P of 1.4 to 1.8, on the layer containing a calcium phosphate powder formed in the above-described step (a); and step (d) of producing a calcium phosphate molded article by jetting an organic acid solution having a pH of 3.5 or lower and including an organic acid whose calcium salt has a solubility in water of 1 g/100 mL or less, through a nozzle unit into a liquid droplet state, and thereby dropping the organic acid solution onto the layer containing a calcium phosphate powder formed in the above-described step (c).

<4> The method for producing a calcium phosphate molded article according to <3>, wherein the organic acid used in the above-described step (d) is at least one selected from the group consisting of citric acid, oxalic acid, tartaric acid, malonic acid, and malic acid.

<5> The method for producing a calcium phosphate molded article according to any one of <1> to <4>, wherein the calcium phosphate powder includes a first calcium phosphate powder and a second calcium phosphate powder, and the solubility of the first calcium phosphate powder in the organic acid is higher than the solubility of the second calcium phosphate powder in the organic acid, and the calcium phosphate powder including the first calcium phosphate powder and the second calcium phosphate powder includes at least particles having a particle size of 5 to 15 μm and particles having a particle size of 25 to 100 the calcium phosphate powder including particles having a particle size of 25 μm or more at a proportion of 20% or higher by volume.

<6> The method for producing a calcium phosphate molded article according to <5>, wherein the flow function of the first calcium phosphate powder is less than 4.00, and the flow function of the calcium phosphate powder including the first calcium phosphate powder and the second calcium phosphate powder is 4.00 or greater, provided that the flow function is represented by the formula: σ1/fc, where fc represents breaking strength, and σ1 represents the maximum principal stress.

<7> The method for producing a calcium phosphate molded article according to any one of <1> to <6>, wherein the concentration of the organic acid solution in step (b) and/or step (d) is from 1.1 mol/L to 1.4 mol/L.

<8> The method for producing a calcium phosphate molded article according to <7>, wherein the organic acid in step (b) and/or step (d) is citric acid.

<9> The method for producing a calcium phosphate molded article according to <7> or <8>, wherein the coating amount of the organic acid solution in step (b) and/or step (d) is from 0.20 g/cm$^3$ to 0.30 g/cm$^3$.

<10> The method for producing a calcium phosphate molded article according to any one of <1> to <9>, wherein the pH of the organic acid solution in step (b) and/or step (d) is from 2.5 to 3.5.

<11> The method for producing a calcium phosphate molded article according to any one of <1> to <10>, further comprising step (e) of removing the proportion of the calcium phosphate powder that has not been used for the formation of the molded article.

<12> The method for producing a calcium phosphate molded article according to <11>, further comprising, after the above-described step (e), step (f) of hardening the molded article by immersing the molded article in an aqueous solution, and/or step (g) of hardening the molded article by heating the molded article.

<13> The method for producing a calcium phosphate molded article according to any one of <1> to <12>, further comprising step (h) of coating the molded article with a biocompatible polymer.

<14> The method for producing a calcium phosphate molded article according to <13>, wherein the biocompatible polymer is a recombinant gelatin.

<15> The method for producing a calcium phosphate molded article according to <13> or <14>, further comprising, after the above-described step (h), step (i) of inoculating cells onto the biocompatible polymer.

<16> The method for producing a calcium phosphate molded article according to any one of <1> to <15>, wherein the calcium phosphate molded article is a scaffold material for regenerative medicine or a tissue repair material.

<17> A calcium phosphate molded article produced by the method for producing a calcium phosphate molded article according to any one of <1> to <16>.

<18> The calcium phosphate molded article according to <17>, wherein the calcium phosphate molded article is a scaffold material for regenerative medicine or a tissue repair material.

<19> The calcium phosphate molded article according to <17> or <18>, comprising holes communicating with the external space.

<20> The calcium phosphate molded article according to <19>, wherein each of the holes communicating with the external space penetrates through the interior of the molded article and communicates with the external space at both ends of the hole.

<21> The calcium phosphate molded article according to <19> or <20>, wherein the average diameter of the holes communicating with the external space is 200 μm to 2,000 μm.

<22> A calcium phosphate molded article formed from a calcium phosphate having a ratio of the numbers of atoms of Ca/P of 1.4 to 1.8, the calcium phosphate molded article comprising primary holes communicating with the external space; and secondary holes having a larger average diameter than the primary holes.

<23> The calcium phosphate molded article according to <22>, wherein the primary holes communicating with the external space have an average diameter of 200 μm to 2,000 μm.

<24> The calcium phosphate molded article according to <22> or <23>, wherein the number of the primary holes communicating with the external space is larger than the number of the secondary holes having a larger average diameter than the primary holes.

<25> A material for transplantation, comprising a calcium phosphate molded article having a surface partially or entirely coated with a recombinant gelatin.

<26> The material for transplantation according to <25>, wherein the calcium phosphate has a ratio of the numbers of atoms of Ca/P of 1.4 to 1.8.

<27> The material for transplantation according to <25> or <26>, wherein the recombinant peptide is thermally crosslinked or chemically crosslinked.

<28> The material for transplantation according to any one of <25> to <27>, wherein the surface of the calcium phosphate molded article coated with recombinant peptide exists on the surface and in the interior of the material for transplantation.

<29> The material for transplantation according to any one of <25> to <28>, wherein the calcium phosphate molded article is block-shaped.

<30> The material for transplantation according to any one of <25> to <28>, wherein the calcium phosphate molded article is granular.

<31> A calcium phosphate molded article formed from calcium phosphate, the molded article having holes communicating with the external space, having a specific gravity of 0.7 g/mL or higher and/or a porosity according to a mercury infusion method of 75% or lower, and having a water absorption infiltration rate of 0.05 min/second or higher:

provided that the water absorption infiltration rate is measured under the following conditions: an experiment system is established, in which one end of a plastic cylinder having an inner diameter of 2 mm is connected to a calcium phosphate molded article having a diameter of 8 mm and a height of 20 mm, the other end of the plastic cylinder is connected to one end of a tube having a length of 100 mm, and the other end of the tube is connected to a 10-mL syringe; under the conditions regulated such that the height at which the calcium phosphate molded article is contacted with the plastic cylinder, and the height of the level of ink contained in the syringe are maintained equal from the initiation to the completion of water absorption and infiltration, the ink in the syringe is subjected to absorption and infiltration into the calcium phosphate molded article; in a case in which the height of the region infiltrated by the ink in the calcium phosphate molded article reaches 15 mm within 5 minutes, a value obtained by dividing 15 mm by the time required for infiltration is defined as the water absorption infiltration rate; and in a case in which the height of the region infiltrated by the ink in the calcium phosphate molded article does not reach 15 mm within 5 minutes, a value obtained by dividing the height of the region infiltrated by the ink in the calcium phosphate molded article at the time point of 5 minutes, by 5 minutes, which is the time required for infiltration, is defined as the water absorption infiltration rate.

<32> The calcium phosphate molded article according to <31>, wherein the calcium phosphate has a ratio of the numbers of atoms of Ca/P of 1.4 to 1.8.

<33> The calcium phosphate molded article according to <31> or <32>, having a structure in which a relatively compact layer and a relatively sparse layer as distinguished by an analysis by nanofocus X-ray CT or microfocus X-ray CT are alternately laminated.

<34> The calcium phosphate molded article according to <33>, wherein at least five or more layers of the relatively compact layer and at least five or more layers of the relatively sparse layer are alternately laminated.

<35> The calcium phosphate molded article according to <33> or <34>, wherein the pitch between a first relatively compact layer and a second relatively compact layer next to the first relatively compact layer is 50 to 300 μm.

<36> The calcium phosphate molded article according to <31> or <32>, wherein in a waveform chart based on a nanofocus X-ray CT image of the calcium phosphate molded article, with the horizontal axis representing the distance in one direction of the molded article and the vertical axis representing the relative CT intensity, peaks and troughs exist alternately.

<37> The calcium phosphate molded article according to <36>, having at least five or more peaks.

<38> The calcium phosphate molded article according to <36> or <37>, wherein the pitch between a first peak and a second peak next to the first peak is 50 to 300 μm.

By employing the method for producing a calcium phosphate molded article according to the invention, a calcium phosphate molded article having high strength can be rapidly produced with high shaping precision. The calcium phosphate molded article of the invention has high strength. The material for transplantation of the invention has excellent cellular adhesiveness and high osteogenesis ability.

DESCRIPTION OF THE PREFERRED EMBODIMENTS

Figure 1:
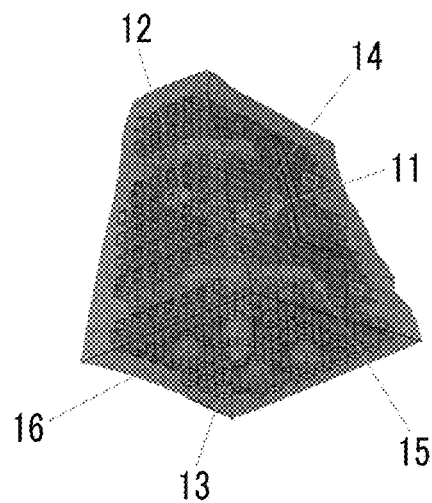
FIG. 1 shows a molded article having X-communicating holes, Y-communicating holes, and Z-communicating holes as primary holes.

In the following description, the present invention will be explained in detail.

The explanation of constituent elements described below is based on representative embodiments of the invention; however, the invention is not intended to be limited to such embodiments.

According to the present specification, a value range described using the symbol "~" means a range including the values described before and after the symbol "~" as the lower limit and the upper limit.

[1] Method for Producing Calcium Phosphate Molded Article

The method for producing a calcium phosphate molded article according to the invention comprises:

step (a) of forming a layer containing a calcium phosphate powder having a ratio of the numbers of atoms of Ca/P of 1.4 to 1.8 on a substrate; and step (b) of producing a calcium phosphate molded article by jetting an organic acid solution having a pH of 3.5 or lower and including an organic acid whose calcium salt has a solubility in water of 1 g/100 mL or less, through a nozzle unit into a liquid droplet state, and thereby dropping the organic acid solution onto the layer containing a calcium phosphate powder formed in step (a).

According to the invention, a calcium phosphate molded article having high strength can be rapidly produced with high shaping precision (high liquid droplet bleeding prevention properties) by using a calcium phosphate powder having a ratio of the numbers of atoms of Ca/P of 1.4 to 1.8 and by using an organic acid solution having a pH of 3.5 or lower and including an organic acid whose calcium salt has a solubility in water of 1 g/100 mL or less. Regarding the mechanism by which the effects of the invention are obtained, the following mechanism is assumed to be effective; however, the scope of the invention is not intended to be limited by the following mechanism.

At or below pH 4, calcium phosphate precipitates as calcium hydrogen phosphate ($CaHPO_4$; also referred to as DCPA) having a ratio of the numbers of atoms of Ca/P of 1. In this invention, an organic acid solution having a pH of 3.5 or lower is used; however, this is because, due to the pH change after jetting, specifically, since calcium phosphate precipitates as DCPA having a ratio of the numbers of atoms of Ca/P of 1, Ca is left over, and the pH is shifted to the alkaline side. At this time, excess Ca is solidified as a salt with lower solubility, and thus it is assumed that effects such as "high hardening rate", "high strength of a molded article", and "precision enhancement of a molded article brought by prevention of bleeding of liquid droplets" are achieved.

The phrase "calcium phosphate molded article having high strength" as used in the present specification means that a calcium phosphate molded article has a strength to the extent that can withstand handling after molding (for example, an operation of taking out the molded article from an apparatus).

<1> Calcium Phosphate Powder

In regard to the calcium phosphate in the calcium phosphate powder used for the invention, the ratio of the numbers of atoms of Ca/P is 1.4 to 1.8. The ratio of the numbers of atoms of Ca/P is preferably 1.45 to 1.79, and more preferably 1.50 to 1.70.

The method for producing a calcium phosphate powder having a ratio of the numbers of atoms of Ca/P of 1.4 to 1.8 is not particularly limited; however, for example, a calcium phosphate powder having a ratio of the numbers of atoms of Ca/P of 1.4 to 1.8 can be produced by using two or more kinds of calcium phosphate powders having known ratios of the numbers of atoms of Ca/P as raw materials, and mixing the two or more kinds of calcium phosphate powders at a predetermined ratio such that the ratio of the numbers of atoms of Ca/P is adjusted to 1.4 to 1.8. For example, a calcium phosphate powder having a ratio of the numbers of atoms of Ca/P of 1.4 to 1.8 can be produced by using $Ca_4(PO_4)_2O$ (tetracalcium phosphate: also referred to as TTCP; the ratio of the numbers of atoms of Ca/P is 2.0) and $CaHPO_4 \cdot 2H_2O$ (calcium hydrogen phosphate dihydrate: also referred to as DCPD; the ratio of the numbers of the atoms of Ca/P is 1.0) as raw materials of the calcium phosphate powders, and varying the mixing ratio of TTCP and DCPD.

The particle size of the powder is such that a smaller particle size is superior in view of reactivity; however, from the viewpoint of making the formation of a powder layer easier, the particle size is preferably 1 μm to 100 μm, more preferably 5 μm to 50 μm, and even more preferably 10 μm to 30 μm. The particle size can be measured by a laser diffraction scattering type particle size distribution analysis method, and specifically, the particle size can be measured using a laser diffraction scattering type particle size distribution analyzer/manufactured by Horiba, Ltd./LA-920 or LMS-2000e manufactured by Seishin Enterprise Co., Ltd.

Preferably, the calcium phosphate powder includes a first calcium phosphate powder and a second calcium phosphate powder, and the solubility of the first calcium phosphate powder in an organic acid (will be described below) is higher than the solubility of the second calcium phosphate powder in an organic acid (will be described below).

Preferably, the calcium phosphate powder including a first calcium phosphate powder and a second calcium phosphate powder includes at least particles having a particle size of 5 to 15 µm and particles having a particle size of 25 to 100 µm, and includes particles having a particle size of 5 to 15 µm at a proportion of 5.0% or more (more preferably 10% or more, and even more preferably 15% or more) by volume and particles having a particle size of 25 µm or greater at a proportion of 20% or more (more preferably 25% or more, and even more preferably 30% or more) by volume.

Preferably, the flow function of the first calcium phosphate powder is lower than 4.00, and the flow function of the calcium phosphate powder including the first calcium phosphate powder and the second calcium phosphate powder is 4.00 or higher. Here, the flow function is represented by the formula: $\sigma1/fc$, wherein fc represents the breaking strength, and $\sigma1$ represents the maximum principal stress. The flow function can be measured according to the description of Examples given below, using a measuring apparatus such as "Powder Flow Tester, PFT" manufactured by Ametek Brookfield, Inc.

<2> Step (a) of Forming Layer Containing Calcium Phosphate Powder on Substrate

Step (a) according to the invention is a step of forming a layer containing a calcium phosphate powder on a substrate.

There are no particular limitations on the material, shape, and size of the substrate, and any appropriate substrate can be used according to the purpose. Regarding the substrate, a substrate having a flat surface with a predetermined area is preferred. The surface area of the substrate is not particularly limited; however, the surface area is preferably 5 to 200 $cm^2$, and more preferably 20 to 100 $cm^2$.

Examples of the material for the substrate include plastic materials such as acrylics, methacrylics (polymethyl methacrylate resin, and the like), polystyrene, and polypropylene; inorganic materials such as glass; and metal materials such as copper, aluminum, and stainless steel.

The step of forming a layer containing a calcium phosphate powder on a substrate can be carried out by any arbitrary method, and the method is not particularly limited. However, for example, the step can be carried out using a 3D printer (three-dimensional printer). As an example of the 3D printer, Z-Printer 310 Plus (3D Systems Corporation (formerly known as Z Corporation)) can be used; however, there are no particular limitations.

<3> Organic Acid Solution

According to the invention, an organic acid solution having a pH of 3.5 or lower and including an organic acid whose calcium salt has a solubility in water of 1 g/100 mL or less is used. The solubility of a calcium salt of an organic acid means solubility at a temperature of 25° C.

In regard to the organic acid solution, the solubility of calcium salt of the organic acid in water is desirably 1 g/100 mL or less; however, the solubility is preferably 0.5 g/100 mL or less, and more preferably 0.1 g/100 mL or less.

The organic acid satisfying the requirement of solubility as described above is preferably at least one selected from the group consisting of citric acid, oxalic acid, tartaric acid, malonic acid, and malic acid, and the organic acid is more preferably citric acid, oxalic acid, or tartaric acid, and even more preferably citric acid.

The pH of the organic acid solution is 5 or lower, preferably 1.0 to 3.5, more preferably from 2.5 to 3.5, and even more preferably from 3.0 to 3.5.

An organic acid solution having a pH of 3.5 or lower can be produced by adjusting the mixing ratio of the organic acid and a salt of the organic acid (sodium salt of the organic acid, or the like).

The concentration of the organic acid in the organic acid solution is not particularly limited; however, the concentration is generally from 0.1 mol/L to 5.0 mol/L, preferably from 0.5 mol/L to 3.0 mol/L, even more preferably from 1.0 mol/L to 2.0 mol/L, and still more preferably from 1.1 mol/L to 1.4 mol/L.

<4> Step (b) of Producing Calcium Phosphate Molded Article Including Jetting of Organic Acid Solution According to the invention, a calcium phosphate molded article is produced by jetting an organic acid solution through a nozzle unit into a liquid droplet state and thereby dropping the organic acid solution onto the layer containing a calcium phosphate powder formed in step (a).

According to the invention, the organic acid solution is jetted out in a liquid droplet state. The liquid droplet state is a state in which the organic acid solution that has been jetted out through a nozzle unit moves around in a space without being brought into contact with any of the nozzle unit and the layer containing a calcium phosphate powder on the substrate.

According to the invention, the temperature employed at the time of jetting out the organic acid solution into a liquid droplet state is not particularly limited; however, the temperature is generally from 15° C. to 50° C., and preferably from 20° C. to 40° C. For example, the temperature is room temperature.

Ejection of the organic acid solution can be carried out using an inkjet head having a nozzle unit. There is known an inkjet recording apparatus that forms an image on a medium by jetting ink droplets from the nozzle unit by means of an actuator of a piezoelectric element or the like, and causing the ink droplets to land on the medium. In an inkjet recording apparatus, the arrangement pitch of the nozzle unit can be made highly dense, and minute ink droplets having a volume of several picoliters to 100 picoliters can be jetted out. A method and apparatus for producing a functional material by an inkjet system are described in JP2012-4555A, and jetting of the organic acid solution can be carried out using the inkjet head described in JP2012-4555A. The entire disclosure of JP2012-4555A is to be incorporated herein by reference.

It is preferable that the inkjet head is configured to be freely movable in the horizontal direction. The inkjet head may be moved with respect to a fixed substrate, or both the inkjet head and the substrate may be moved. The inkjet head is intended to jet out an ink (that is, organic acid solution) supplied from an ink tank onto a desired position of a layer containing a powder on a substrate.

The inkjet system may be any of a continuous type system and an on-demand type system; however, in the case of jetting ink droplets onto a large area that measures several ten cm or more on each of four sides, the on-demand type employing a large number of nozzles is preferred. Regarding the actuator that characterizes an on-demand type jetting system, various systems such as a piezoelectric system, a thermal system, a solid system, and an electrostatic suction system can be used. A piezoelectric system is also capable of jetting an organic solvent-based ink, in addition to a water-based ink. The layout of nozzles may be any of disposition in a single row, disposition in a plurality of rows, and disposition in a houndstooth check pattern.

The above-described step (b) of producing a calcium phosphate molded article including jetting of an organic acid solution can be carried out using, for example, a 3D printer (three-dimensional printer) equipped with an inkjet head. As an example of the 3D printer, Z-Printer 310 Plus (3D Systems Corporation (formerly known as Z Corporation) or the like can be used; however, there are no particular limitations.

The size of the calcium phosphate molded article produced by the method of the invention is not particularly limited; however, in a case in which the calcium phosphate molded article is approximated into a cuboid, the width, length, and height of the cuboid are respectively preferably 0.1 mm to 200 mm, and more preferably 1 mm to 100 mm.

<5> Lamination

The method for producing a calcium phosphate molded article according to the invention may further comprise, after the step (b), step (c) of forming a layer containing a calcium phosphate powder having a ratio of the numbers of atoms of Ca/P of 1.4 to 1.8 on the layer containing a calcium phosphate powder formed in step (a); and step (d) of producing a calcium phosphate molded article by jetting an organic acid solution having a pH of 3.5 or lower and including an organic acid whose calcium salt has a solubility in water of 1 g/100 mL or less, through a nozzle unit into a liquid droplet state, and thereby dropping the organic acid solution onto the layer containing a calcium phosphate powder formed in step (c).

The above-described step (c) can be carried out in the same manner as in step (a). The types of the materials used in step (c) may be identical with or different from the materials used in step (a); however, it is preferable that the materials are identical.

The above-described step (d) can be carried out in the same manner as in step (b). The types of the materials used in step (d) may be identical with or different from the materials used in step (b); however, it is preferable that the materials are identical.

The organic acid used in step (d) is, similarly to the case of step (b), preferably at least one selected from the group consisting of citric acid, oxalic acid, tartaric acid, malonic acid, and malic acid; more preferably citric acid, oxalic acid, or tartaric acid; and even more preferably citric acid.

In the case of carrying out step (c) and step (d), the number of time is not particularly limited, and the steps can be carried out at any arbitrary number of times such as one or more times. For example, the steps can be carried out one time to 1,000 times.

The coating amount of the organic acid solution in step (b) and/or step (d) is generally from 0.10 g/cm$^3$ to 0.40 g/cm$^3$, and preferably from 0.20 g/cm$^3$ to 0.30 g/cm$^3$.

<6> Step of Removing Calcium Phosphate Powder

According to the invention, step (e) of removing any calcium phosphate powder that has not been used for the formation of the molded article can be further provided. Removing a calcium phosphate powder means removing a calcium phosphate powder from the surface of the molded article.

By removing any calcium phosphate powder that has not been used for the formation of a molded article, a molded article molded into a desired shape can be collected. According to the invention, since the molded article thus formed has predetermined strength, any calcium phosphate powder that has not been used for the formation of the molded article can be removed without damaging the molded article.

The method for removing any calcium phosphate powder that has not been used for the formation of the molded article is not particularly limited, and for example, the removal may be carried out using compressed air.

<7> Step of Hardening Molded Article

According to the invention, step (f) of hardening the molded article by immersing the molded article in an aqueous solution, and/or step (g) of hardening the molded article by heating the molded article can be further provided, after step (e) of removing any calcium phosphate powder that has not been used for the formation of the molded article. However, step (f) and step (g) may be respectively provided or may not be provided.

By carrying out step (f) and/or step (g) described above, the added organic acid can be removed, and the strength of the molded article can be further increased.

Furthermore, in the case of carrying out step (c) and step (d) described above (that is, in the case of laminating layers containing a calcium phosphate powder), the strength of the molded article can be further increased by hardening the molded article by step (f). It is speculated that the strength of the molded article can be further increased due to an enhancement of the strength between the layers containing a calcium phosphate powder. That is, according to a preferred embodiment of the invention, after step (a) and step (b) are carried out, step (c) and step (d) are carried out, and then step (e) of removing any calcium phosphate powder that has not been used for the formation of the molded article is carried out. Furthermore, after step (e), step (f) of hardening the molded article can be carried out by immersing the molded article in an aqueous solution.

The type of the aqueous solution used in step (f) of hardening the molded article by immersing the molded article in an aqueous solution is not particularly limited as long as the aqueous solution can harden the molded article, and examples include an aqueous solution of phosphoric acid. More specifically, a sodium dihydrogen phosphate solution at 0.1 mol/L to 1.0 mol/L or the like can be used. The pH of the aqueous solution is not particularly limited; however, the pH is generally pH 3 to 11, preferably pH 3 to 10, and more preferably pH 4 to 9.

The time for immersing the molded article in an aqueous solution is not particularly limited; however, the time is generally from 1 hour to 48 hours, preferably from 2 hours to 24 hours, and more preferably from 4 hours to 24 hours.

Step (g) of hardening the molded article by heating the molded article can be carried out by heating the molded article generally at a temperature of 100° C. to 2,000° C., preferably 200° C. to 1,500° C., more preferably 500° C. to 1,500° C., even more preferably 1,000° C. to 1,300° C., and particularly preferably 1,100° C. to 1,200° C. Meanwhile, T [Kelvin: K]=t [degree Celsius: ° C.]+273.15.

The heating time is not particularly limited; however, the heating time is generally from 1 hour to 48 hours, preferably from 1 hour to 24 hours, more preferably from 2 hours to 12 hours, and even more preferably from 2 hours to 6 hours.

Heating can be carried out by a conventional method using a muffle furnace or the like.

By carrying out step (f) and/or step (g) of hardening the molded article described above, the compressive strength of the molded article can be increased. The compressive strength of the molded article that has been subjected to step (f) and/or step (g) is not particularly limited; however, the compressive strength is preferably 2.5 MPa or higher, more preferably 3.0 MPa or higher, and even more preferably 3.5 MPa or higher. The upper limit of the compressive strength is not particularly limited; however, the upper limit is generally 10 MPa or lower.

<8> Step of Coating Biocompatible Polymer

According to the invention, step (h) of coating the molded article with a biocompatible polymer can be further provided. However, step (h) may or may not be provided. By coating the molded article with a biocompatible polymer, adsorption of cells can be made easier. Preferably, the molded article is coated with a biocompatible polymer (preferably, a recombinant gelatin described below) after acid is removed from the molded article by carrying out step (f) and/or step (g) of hardening the molded article as described above in the present specification, and thereby a reaction between the biocompatible polymer and the acid can be prevented. That is, according to a preferred embodiment of the invention, step (h) of coating the molded article with a biocompatible polymer can be carried out after step (f) and/or step (g) of hardening the molded article is carried out.

(8-1) Biocompatible Polymer

Biocompatibility means that in a case in which a material is brought into contact with a living body, the material does not induce any noticeable harmful reaction such as a long-term chronic inflammatory reaction. Regarding the biocompatible polymer, there are no particular limitations on whether the polymer is degradable in vivo, as long as the polymer is biologically compatible; however, a biodegradable polymer is preferred. Specific examples of a non-biodegradable material include polytetrafluoroethylene (PTFE), polyurethane, polypropylene, polyester, vinyl chloride, polycarbonate, acrylic, stainless steel, titanium, silicone, and MPC (2-methacryloyloxyethyl phosphorylcholine). Specific examples of a biodegradable material include polypeptides such as a naturally occurring peptide, a recombinant peptide (RCP), and a chemically synthesized peptide (for example, gelatin that will be described below); polylactic acid, polyglycolic acid, a lactic acid-glycolic acid copolymer (PLGA), hyaluronic acid, glycosaminoglycan, proteoglycan, chondroitin, cellulose, agarose, carboxymethyl cellulose, chitin, and chitosan. Among the materials described above, a recombinant peptide is particularly preferred. These biocompatible polymers may be designed to increase cellular adhesiveness. Specifically, methods such as "coating of a base material surface with cell adhesion substrates (fibronectin, vitronectin, and laminin) or cell adhesion sequence (represented by single-letter amino acid codes, RGD sequence, LDV sequence, REDV sequence, YIGSR sequence, PDSGR sequence, RYVVLPR sequence, LGTIPG sequence, RNIAEIIKDI sequence, IKVAV sequence, LRE sequence, DGEA sequence, and HAV sequence) peptides", "amination and cationization of a base material surface", and "plasma treatment and corona discharge-induced hydrophilization treatment of a base material surface" can be used.

The type of the polypeptide including a recombinant peptide or a chemically synthesized peptide is not particularly limited as long as the polypeptide is biocompatible; however, preferred examples include gelatin, collagen, elastin, fibronectin, ProNectin, laminin, tenascin, fibrin, fibroin, entactin, thrombospondin, and retronectin, while most preferred examples include gelatin, collagen, and atelocollagen. The gelatin used for the invention is preferably natural gelatin, a recombinant gelatin, or a chemically synthesized gelatin, and more preferably a recombinant gelatin. Natural gelatin means gelatin produced from naturally occurring collagen. The living organism from which gelatin is derived is not particularly limited, and for example, gelatin derived from an animal (a mammal, a fish, or the like) can be used.

A chemically synthesized peptide or chemically synthesized gelatin means an artificially synthesized peptide or gelatin. Synthesis of a peptide such as gelatin may be solid phase synthesis or liquid phase synthesis; however, solid phase synthesis is preferred. Solid phase synthesis of a peptide is known to those ordinarily skilled in the art, and examples include an Fmoc group synthesis method of using an Fmoc group (Fluorenyl-Methoxy-Carbonyl group) for the protection of an amino group, and a Boc group synthesis method of using a Boc group (tert-ButylOxyCarbonyl group) for the protection of an amino group. Regarding a preferred embodiment of chemically synthesized gelatin, the matter described below in connection with the recombinant gelatin in the present specification can be applied.

The recombinant gelatin will be described below in the present specification.

The hydrophilicity value, "1/IOB" value, of a biocompatible polymer is preferably from 0 to 1.0, more preferably from 0 to 0.6, and even more preferably from 0 to 0.4. The IOB is an index of hydrophilicity/hydrophobicity based on an organic conceptual diagram representing the polarity/non-polarity of an organic compound suggested by Atsushi Fujita, and the details are explained in, for example, "Pharmaceutical Bulletin", Vol. 2, 2, pp. 163-173 (1954), "Kagaku no Ryoiki (Realm of Chemistry)", Vol. 11, 10, pp. 719-725 (1957), and "Fragrance Journal", Vol. 50, pp. 79-82 (1981). To be brief, the root of all organic compounds is considered as methane ($CH_4$), other compounds are all regarded as derivatives of methane, and a certain value is assigned to each of the number of carbon atoms, a substituent, a transformed moiety, a ring, or the like of such a derivative. The scores are added up, and an organic value (OV) and an inorganic value (IV) are determined. These values are plotted on a graph, in which the X-axis represents the organic value, and the Y-axis represents the inorganic value. The IOB in an organic conceptual diagram refers to the ratio of the inorganic value (IV) to the organic value (OV) in the organic conceptual diagram, that is, "inorganic value (IV)/organic value (OV)". For the details of the organic conceptual diagram, "Shinpan Yuki Gainenzu—Kiso to Oyo (New Edition of Organic Conceptual Diagram—Fundamentals and Applications" (written by Yoshio Koda et al., Sankyo Shuppan Co., Ltd., 2008) can be referred to. In the present specification, hydrophilicity/hydrophobicity is indicated by the "1/IOB" value, which is a reciprocal of IOB. A smaller "1/IOB" value (close to 0) indicates being more hydrophilic.

In a case in which the biocompatible polymer used for the invention is a polypeptide, the hydrophilicity/hydrophobicity index represented by the Grand average of hydropathicity (GRAVY) value is preferably 0.3 or less and −9.0 or more, and more preferably 0.0 or less and −7.0 or more. The Grand average of hydropathicity (GRAVY) value can be obtained by the methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31:3784-3788 (2003)".

(8-2) Crosslinking

The biocompatible polymer may be crosslinked or may not be crosslinked. Regarding general crosslinking methods, thermal crosslinking, crosslinking by an aldehyde (for example, formaldehyde or glutaraldehyde), crosslinking by a condensing agent (carbodiimide, cyanamide, or the like), enzymatic crosslinking, photocrosslinking, ultraviolet crosslinking, hydrophobic interaction, hydrogen bonding, ionic interaction, and the like are known, and the above-described crosslinking methods can also be used for the invention. The crosslinking method used for the invention is more preferably thermal crosslinking, ultraviolet crosslinking, or enzymatic crosslinking, and particularly preferably thermal crosslinking.

In the case of performing enzyme-induced crosslinking, the enzyme is not particularly limited as long as it has a crosslinking action between polymer materials; however, preferably crosslinking can be carried out using a transglutaminase and a laccase, and most preferably a transglutaminase. Regarding specific examples of a protein that is enzymatically crosslinked by a transglutaminase, there are no particular limitations as long as the protein is a protein having a lysine residue and a glutamine residue. The transglutaminase may be a mammal-derived enzyme or a microorganism-derived enzyme, and specific examples include ACTIVA series manufactured by Ajinomoto Co., Inc.; mammal-derived transglutaminases that are commercially available as reagents, for example, guinea pig liver-derived transglutaminases, goat-derived transglutaminases, and rabbit-derived transglutaminases manufactured by Oriental Yeast Co., Ltd., Upstate USA, Inc., and Biodesign International, Inc., and the like; and human-derived blood coagulation factors (Factor XIIIa, Haematologic Technologies, Inc.).

The reaction temperature employed at the time of performing crosslinking (for example, thermal crosslinking) is not particularly limited as long as crosslinking is enabled; however, the reaction temperature is preferably −100° C. to 500° C., more preferably 0° C. to 300° C., even more preferably 50° C. to 300° C., still more preferably 100° C. to 250° C., and still more preferably 120° C. to 200° C.

(8-3) Recombinant Gelatin

The gelatin used for the invention is preferably a recombinant gelatin.

A recombinant gelatin means a polypeptide or protein-like substance having an amino acid sequence similar to that of gelatin, which has been produced by a gene recombination technology. It is preferable that the recombinant gelatin that can be used for the invention has repetitions of a sequence represented by Gly-X-Y (wherein X and Y each independently represent any one amino acid), which is characteristic to collagen. Herein, a plurality of the sequences Gly-X-Y may be respectively identical or different. Preferably, two or more sequences of a cell adhesion signal are incorporated into one molecule. Regarding the recombinant gelatin used for the invention, a recombinant gelatin having an amino acid sequence derived from a partial amino acid sequence of collagen can be used. For example, the recombinant gelatins described in EP1014176B, U.S. Pat. No. 6,992,172B, WO2004/85473A, and WO2008/103041A can be used; however, the recombinant gelatin is not limited to these. A preferred recombinant gelatin to be used for the invention is a recombinant gelatin of the following embodiment.

A recombinant gelatin has excellent biocompatibility due to the performance intrinsic to natural gelatin, has no risk of bovine spongiform encephalopathy (BSE) or the like because it is not naturally derived, and is highly non-infectious. Furthermore, since a recombinant gelatin is uniform compared to natural gelatin and has a defined sequence, it is possible to design the recombinant gelatin, in terms of strength and degradability, with precision and with reduced fluctuation by crosslinking or the like.

The molecular weight of the recombinant gelatin is not particularly limited; however, the molecular weight is preferably from 2,000 to 100,000 (from 2 kDa (kilodaltons) to 100 kDa), more preferably from 2,500 to 95,000 (from 2.5 kDa to 95 kDa), even more preferably from 5,000 to 90,000 (from 5 kDa to 90 kDa), and most preferably from 10,000 to 90,000 (from 10 kDa to 90 kDa).

It is preferable that the recombinant gelatin has repetitions of a sequence represented by Gly-X-Y, which is characteristics to collagen. Herein, a plurality of the sequences Gly-X-Y may be respectively identical or different. In Gly-X-Y, Gly represents glycine, and X and Y each represent an arbitrary amino acid (preferably, any arbitrary amino acid other than glycine). A sequence represented by Gly-X-Y characteristic to collagen is a very specific partial structure compared to other proteins, in the amino acid compositions and sequences of gelatin and collagen. In this moiety, glycine occupies about one-third of the whole sequence, and in the amino acid sequence, glycine is repeated at a rate of one in three. Glycine is the simplest amino acid, is subject to less restraint in the disposition in a molecular chain, and significantly contributes to regeneration of a helical structure upon gelation. It is preferable that the amino acids represented by X and Y include a large proportion of imino acids (proline and oxyproline), which occupy 10% to 45% of the whole amount. Preferably, 80% or more, more preferably 95% or more, and most preferably 99% or more of the amino acids in the sequence of the recombinant gelatin constitute a repeated structure of Gly-X-Y.

General gelatin is such that among polar amino acids, charged ones and uncharged ones exist at a ratio of 1:1. Herein, polar amino acids specifically refer to cysteine, aspartic acid, glutamic acid, histidine, lysine, asparagine, glutamine, serine, threonine, tyrosine, and arginine, and among these, uncharged polar amino acids refer to cysteine, asparagine, glutamine, serine, threonine, and tyrosine. In the recombinant gelatin used for the invention, the proportion of polar amino acids among all the constituent amino acids is 10% to 40%, and preferably 20% to 30%. The proportion of uncharged amino acids in the polar amino acids is preferably 5% or more and less than 20%, and more preferably 5% or more and less than 10%. Furthermore, it is preferable that the recombinant gelatin does not include any one amino acid among serine, threonine, asparagine, tyrosine, and cysteine on the sequence, and it is more preferable that the recombinant gelatin does not include two or more amino acids among serine, threonine, asparagine, tyrosine, and cysteine on the sequence.

Generally, in regard to polypeptides, minimum amino acid sequences that work as cell adhesion signals are known (for example, "Byotai Seiri (Pathologic physiology)" published by Nagai Shuppan K. K., Vol. 9, No. 7 (1990), p. 527). It is preferable that the recombinant gelatin used for the invention has two or more of these cell adhesion signals in one molecule. Regarding specific sequences, from the viewpoint that there are many types of adhering cells, the sequences of an RGD sequence, an LDV sequence, a REDV sequence, a YIGSR sequence, a PDSGR sequence, an RYVVLPR sequence, an LGTIPG sequence, an RNIAEIIKDI sequence, an IKVAV sequence, an LRE sequence, a DGEA sequence, and an HAV sequence, which are represented by single-letter amino acid codes, are preferred. More preferred are an RGD sequence, a YIGSR sequence, a PDSGR sequence, an LGTIPG sequence, an IKVAV sequence, and an HAV sequence, and particularly preferred is an RGD sequence. Among RGD sequences, an ERGD sequence is preferred. By using a recombinant gelatin having a cell adhesion signal, the substrate production amount of cells can be increased.

Regarding the disposition of RGD sequences in the recombinant gelatin used for the invention, it is preferable that the number of amino acids between RGD sequences is not uniform between 0 and 100, and it is more preferable that the number of amino acids between RGD sequences is not uniform between 25 and 60.

From the viewpoints of cellular adhesion and proliferation, the content of this minimum amino acid sequence is preferably 3 to 50 sequences, more preferably 4 to 30 sequences, and particularly preferably 5 to 20 sequences in one molecule of protein. The most preferred content is 12 sequences.

In regard to the recombinant gelatin used for the invention, the proportion of RGD motif with respect to the total number of amino acids is preferably at least 0.4%. In a case in which the recombinant gelatin includes 350 or more amino acids, it is preferable that each stretch of the 350 amino acids includes at least one RGD motif. The proportion of RGD motif with respect to the total number of amino acids is more preferably at least 0.6%, even more preferably at least 0.8%, still more preferably at least 1.0%, particularly preferably at least 1.2%, and most preferably at least 1.5%. The number of RGD motifs in the recombinant peptide is preferably at least 4, more preferably 6, even more preferably 8, and particularly preferably from 12 to 16, per 250 amino acids. The proportion of 0.4% of the RGD motif is equivalent to at least one RGD sequence per 250 amino acids. Since the number of the RGD motif is an integer, in order to satisfy the characteristic of 0.4%, gelatin comprising 251 amino acids must include at least two RGD sequences. Preferably, the recombinant gelatin of the invention includes at least two RGD sequences per 250 amino acids; more preferably includes at least three RGD sequences per 250 amino acids; and even more preferably includes at least four RGD sequence per 250 amino acids. Still another embodiment of the recombinant gelatin of the invention includes at least four RGD motifs, preferably 6, more preferably 8, and even more preferably from 12 to 16 RGD motifs.

The recombinant gelatin may be partially hydrolyzed.

Preferably, the recombinant gelatin used for the invention is represented by the formula: A-[(Gly-X-Y)$_n$]$_m$—B. n units of X each independently represent any one amino acid, and n units of Y each independently represent any one amino acid. m represents an integer from 2 to 10, and more preferably an integer from 3 to 5. n is preferably an integer from 3 to 100, more preferably an integer from 15 to 70, and most preferably an integer from 50 to 65. A represents an arbitrary amino acid or amino acid sequence, and B represents an arbitrary amino acid or amino acid sequence. Meanwhile, n units of Gly-X-Y may be respectively identical or different.

More preferably, the recombinant gelatin used for the invention is represented by the formula: Gly-Ala-Pro-[(Gly-X-Y)$_{63}$]$_3$-Gly (wherein 63 units of X each independently represent any one amino acid; 63 units of Y each independently represent any one amino acid; and 63 units of Gly-X-Y may be respectively identical or different).

For the repeating unit, it is preferable that a plurality of sequence units of naturally occurring collagen is linked. The naturally occurring collagen as used herein may be any collagen as long as it exists in nature; however, the collagen is preferably Type I, Type II, Type III, Type IV, or Type V collagen. The collagen is more preferably Type I, Type II, or Type III collagen. According to another embodiment, the above-described collagen is preferably derived from human being, cattle, pig, mouse, or rat, and more preferably derived from human being.

The isoelectric point of the recombinant gelatin used for the invention is preferably 5 to 10, more preferably 6 to 10, and even more preferably 7 to 9.5. Measurement of the isoelectric point of the recombinant gelatin can be carried out by passing a 1 mass % gelatin solution through a mixed bed column of cation and anion exchange resins and then measuring the pH, as described in Isoelectric Point Electrophoresis Method (see Maxey, C. R. (1976); Phitogr. Gelatin 2, Editor Cox, P. J. Academic, London, Engl.).

Preferably, the recombinant gelatin is not deaminated.

Preferably, the recombinant gelatin does not have a telopeptide.

Preferably, the recombinant gelatin is a substantially pure polypeptide produced by a nucleic acid encoding an amino acid sequence.

The recombinant gelatin used for the invention is particularly preferably any one of the following:

(1) a peptide comprising an amino acid sequence set forth in SEQ ID NO:1;

(2) a biocompatible peptide comprising an amino acid sequence having one or several amino acids deleted, substituted or added in the amino acid sequence set forth in SEQ ID NO:1; and (3) a biocompatible peptide comprising an amino acid sequence having at least 80% (more preferably at least 90%, particularly preferably at least 95%, and most preferably at least 98%) sequence identity with the amino acid sequence set forth in SEQ ID NO:1.

The sequence identity according to the invention refers to a value calculated by the following formula:

% Sequence identity=[(Number of identical residues)/(alignment length)]×100

The sequence identity of two amino acid sequences can be determined by any method known to those ordinarily skilled in the art and can be determined using BLAST ((Basic Local Alignment Search Tool)) program (J. Mol. Biol. 215:403-410, 1990).

The phrase "one or several" in the "amino acid sequence having one or several amino acids deleted, substituted, or added" means preferably 1 to 20 amino acids, more preferably 1 to 10 amino acids, even more preferably 1 to 5 amino acids, and particularly preferably 1 to 3 amino acids.

The recombinant gelatin used for the invention can be produced by a gene recombination technology known to those ordinarily skilled in the art, and the recombinant gelatin can be produced according to the methods described in, for example, EP1014176A2, U.S. Pat. No. 6,992,172B, WO2004/85473A, and WO2008/103041A. Specifically, a gene encoding the amino acid sequence of a predetermined recombinant gelatin is obtained, this is incorporated into an expression vector, and thereby a recombinant expression vector is produced. This is introduced into an appropriate host, and thus a transformant is produced. The transformant thus obtained is cultured in an appropriate medium, and thereby a recombinant gelatin is produced. Therefore, the recombinant gelatin to be used for the invention can be produced by collecting the recombinant gelatin produced from the culture.

(8-4) Coating with Biocompatible Polymer

The method of coating a molded article with a biocompatible polymer is not particularly limited; however, a biocompatible polymer solution can be used. The solvent used for the biocompatible polymer solution is not particularly limited as long as it is a solvent capable of dissolving the biocompatible polymer; however, the solvent is generally water, an organic solvent, or a mixture of water and an organic solvent, and preferably water or an aqueous medium such as a mixture of water and an organic solvent. Examples of the organic solvent include acetone and ethanol. In the case of a gelatin solution, preferably, an aqueous solution of gelatin can be used.

The concentration of the biocompatible polymer in the biocompatible polymer solution is not particularly limited; however, the concentration is generally 1% by mass to 50% by mass, preferably 2% to 40% by mass, and more preferably 3% to 30% by mass.

By treating a molded article with the biocompatible polymer solution described above, the molded article can be coated with the biocompatible polymer. Specifically, a molded article can be coated with a biocompatible polymer by immersing the molded article in a biocompatible polymer solution and drying the molded article.

<9> Step of Inoculating Cells onto Biocompatible Polymer

According to the invention, after step (h) of coating the molded article with a biocompatible polymer, step (i) of inoculating cells onto the biocompatible polymer can be further provided.

The use of the molded article according to the invention is intended to be a scaffold material for regenerative medicine, a tissue repair material, or the like as will be described below; however, a case of using the molded article after inoculating cells thereon and a case of using the molded article without inoculating cells thereon are assumed.

The type of the cells to be inoculated is not particularly limited, and cells can be selected as appropriate according to the purpose of use.

The cells to be used are preferably animal cells, more preferably vertebrate-derived cells, and particularly preferably human-derived cells. The type of the vertebrate-derived cells (particularly, human-derived cells) may be any of pluripotent cells, somatic stem cells, precursor cells, and mature cells. Regarding the pluripotent cells, for example, embryonic stem (ES) cells, germline stem (GS) cells, or induced pluripotent stem (iPS) cells can be used. Regarding the somatic stem cells, for example, mesenchymal stem cells (MSC), hematopoietic stem cells, amniotic cells, cord blood cells, bone marrow-derived cells, cardiac stem cells, adipose-derived stem cells, or neural stem cells can be used. Regarding the precursor cells and mature cells, for example, cells derived from skin, dermis, epidermis, muscle, cardiac muscle, neuron, bone, cartilage, endothelium, brain, epithelium, heart, kidney, liver, pancreas, spleen, intraoral, cornea, bone marrow, cord blood, amnion, or hair can be used. Regarding human-derived cells, for example, ES cells, iPS cells, MSC, cartilage cells, osteoblasts, osteoprogenitor cells, mesenchymal cells, myoblasts, cardiac muscle cells, cardiac myoblasts, nerve cells, liver cells, beta cells, fibroblasts, corneal endothelial cells, vascular endothelial cells, corneal epithelial cells, amniotic cells, cord blood cells, bone marrow-derived cells, or hematopoietic cells can be used. The origin of the cells may be any of autologous cells or heterologous cells.

<10> Usage of Calcium Phosphate Molded Article Produced by Method of Invention

There are no particular limitations on the usage of the calcium phosphate molded article produced by the method for producing a calcium phosphate molded article according to the invention; however, preferably the calcium phosphate molded is used as a scaffold material for regenerative medicine or a tissue repair material. The usage of the calcium phosphate molded article will be described below in the present specification.

[2] Calcium Phosphate Molded Article

The invention further provides a calcium phosphate molded article produced by the method for producing a calcium phosphate molded article according to the invention described in the above section [1].

The calcium phosphate molded article of the invention has high strength and can be rapidly produced with high shaping precision.

The invention further provides a calcium phosphate molded article formed from calcium phosphate, the molded article having holes communicating with the external space, having a specific gravity of 0.7 g/mL or higher and/or a porosity according to a mercury infusion method of 75% or lower, and having a water absorption infiltration rate of 0.05 mm/second or higher.

The specific gravity of the calcium phosphate molded article is 0.7 g/mL or higher, preferably 0.75 g/mL or higher, and more preferably 0.85 g/mL or higher.

The porosity according to a mercury infusion method of the calcium phosphate molded article is 75% or lower, more preferably 70% or lower, even more preferably 67% or lower, and particularly preferably 65% or lower.

A mercury intrusion method is a method of applying pressure in order to cause mercury to infiltrate into pores of a powder by utilizing the fact that mercury has high surface tension, and determining the specific surface area or the pore distribution from the pressure and the amount of intruded mercury. Porosity can be measured using an apparatus such as POREMASTER 60GT (manufactured by Quantachrome Corporation).

The water absorption infiltration rate of the calcium phosphate molded article is 0.05 mm/second or higher, preferably 0.10 mm/second or higher, more preferably 0.30 mm/second or higher, even more preferably 0.50 mm/second or higher, still more preferably 0.70 mm/second or higher, still more preferably 0.80 mm/second or higher, and particularly preferably 0.90 mm/second or higher.

It is desirable that the water absorption infiltration rate of the calcium phosphate molded article satisfies the above-described water absorption infiltration rate in at least one direction among the X-direction (drawing direction), Y-direction (recoat scanning direction), and Z-direction (lamination direction). However, it is preferable that the water absorption infiltration rate satisfies the above-described water absorption infiltration rate in any two direction among the directions mentioned above, and it is more preferable that the water absorption infiltration rate satisfies the above-described water absorption infiltration rate in all of the directions described above (three directions).

The water absorption infiltration rate according to the invention is a value measured under the following conditions. The temperature in the laboratory in which measurement is carried out is maintained at 20° C. to 25° C., and the humidity is maintained at 25% to 40%. An experiment system is established, in which one end of a plastic cylinder having an inner diameter of 2 mm is connected to a calcium phosphate molded article having a diameter of 8 mm and a height of 20 mm, the other end of the plastic cylinder is connected to one end of a tube having a length of 100 mm, and the other end of the tube is connected to a 10-mL syringe. Under the conditions adjusted such that the height at which the calcium phosphate molded article is brought into contact with the plastic cylinder and the height of the level of the ink in the syringe are maintained the same from the initiation to the completion of water absorption infiltration, the ink in the syringe is subjected to absorption infiltration into the calcium phosphate molded article. In a case where the height of a region of the calcium phosphate molded article, into which the ink has infiltrated, reaches 15 mm within 5 minutes, a value obtained by dividing 15 mm by the time required for infiltration is designated as the water absorption infiltration rate. In a case where the height of a region of the calcium phosphate molded article, into which ink has infiltrated, does not reach 15 mm within 5 minutes, a value obtained by measuring the height of the region of the calcium phosphate molded article, into which the ink has infiltrated, with a ruler at the time point of 5 minutes and dividing the height by the time required for infiltration, is designated as the water absorption infiltration rate.

In regard to the calcium phosphate in the calcium phosphate molded article, the ratio of the numbers of atoms of Ca/P is preferably 1.4 to 1.8, more preferably 1.45 to 1.79, and even more preferably 1.50 to 1.70.

The calcium phosphate molded article of the invention preferably has a structure in which a relatively compact layer and a relatively sparse layer are alternately laminated. A relatively compact layer and a relatively sparse layer mean layers that can be distinguished as a relatively compact layer and a relatively sparse layer by an analysis by nanofocus X-ray CT or microfocus X-ray CT. The relatively compact layer means that the layer is more compact than the relatively sparse layer, and the relatively sparse layer means that the layer is sparser than the relatively compact layer.

As will be described in the Examples below, a CT analysis of the calcium phosphate molded article is performed, and then the way of viewing white, gray, and black is adjusted using a software program so that the pattern of the internal structure of the calcium phosphate molded article is seen, and that the relatively compact layer and the relatively sparse layer can be recognized. The direction of Ca phosphate is adjusted so that a black and white stripe pattern is made visible, and a direction orthogonally intersecting the black and white stripe pattern is designated as Z-axis, while a direction orthogonally intersecting the Z-axis is designated as the XY plane (the X-axis and the Y-axis are also adjusted to be directions orthogonally intersecting each other). From the ZX plane or the YZ plane, a region in the range of from 0.5 mm to 5.0 mm in the Z-axis direction and in the range of from 0.5 mm to 5.0 mm in the X-axis direction is selected. A waveform can be obtained using a software program by plotting the distance in the Z-axis direction of the selected region on the horizontal axis and the degree of monochromaticity of the selected region on the vertical axis. From the waveform thus obtained, the number of layers and the pitch of the relatively compact layers and the relatively sparse layers can be analyzed.

According to the invention, preferably, at least 5 or more layers (more preferably at least 7 or more layers, and even more preferably at least 10 or more layers) of the relatively compact layer and at least 5 or more layers (more preferably at least 7 or more layers, and even more preferably at least 10 or more layers) of the relatively sparse layer are alternately laminated.

The pitch between a first relatively compact layer and a second relatively compact layer next to the first relatively compact layer is preferably 50 to 300 µm, more preferably 60 to 200 µm, and even more preferably 70 to 150 µm.

As relatively compact layers exist, the external appearance and the internal structure can be formed, and since the relatively compact layers are substituted by cells while being absorbed by the cells, the overall shape can be maintained. As relatively sparse layers exist, a larger amount of cells can infiltrate more rapidly and more broadly. Therefore, by having a structure in which a relatively compact layer and a relatively sparse layer are alternately laminated, there is an advantage that cellular infiltration is made easier, and tissue regeneration is faster, compared to a calcium phosphate molded article that does not have a structure in which a relatively compact layer and a relatively sparse layer are alternately laminated.

Figure 30:
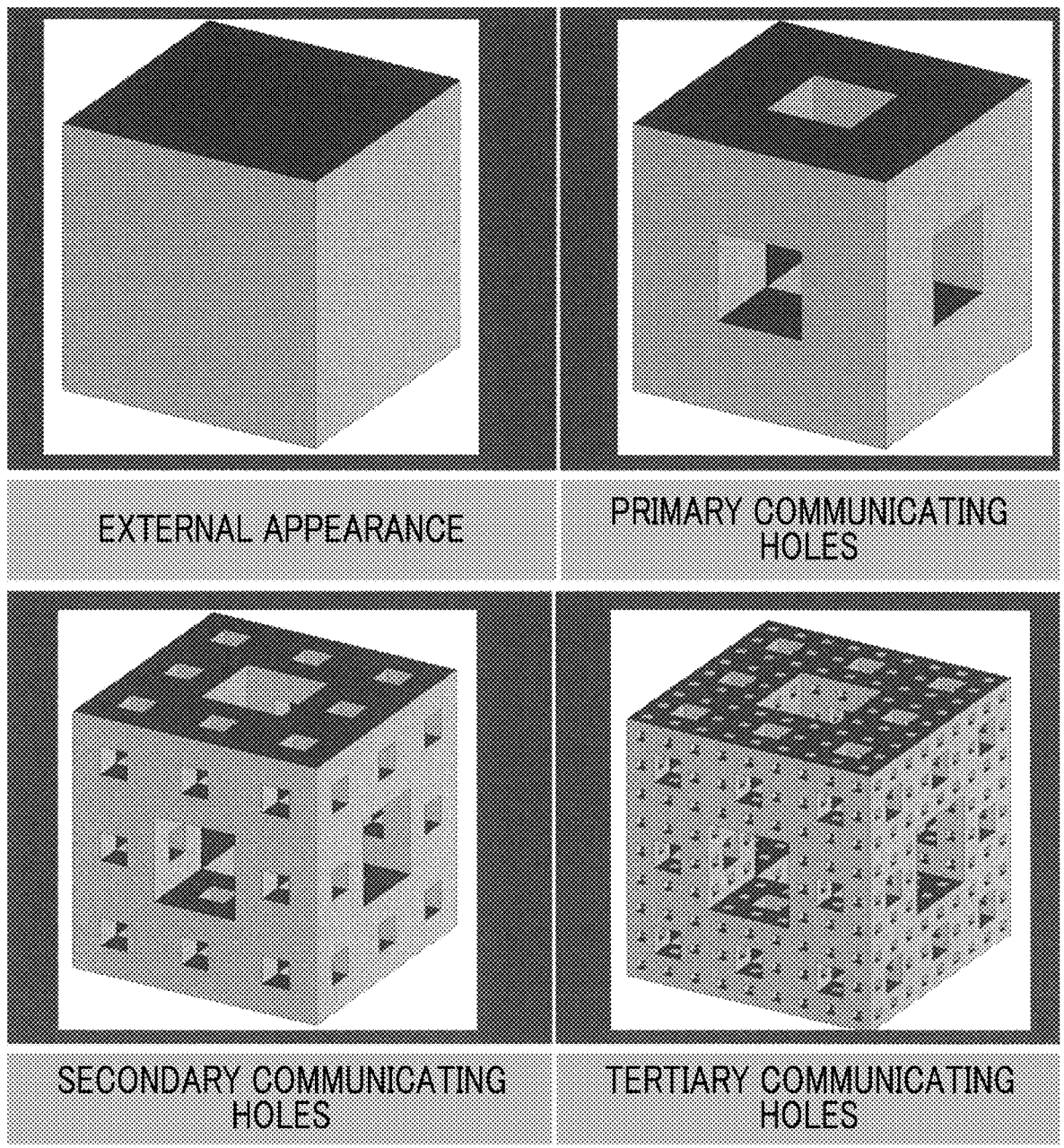
FIG. 30 is a schematic diagram of a calcium phosphate molded article having three phases of communicating holes.
Figure 31:
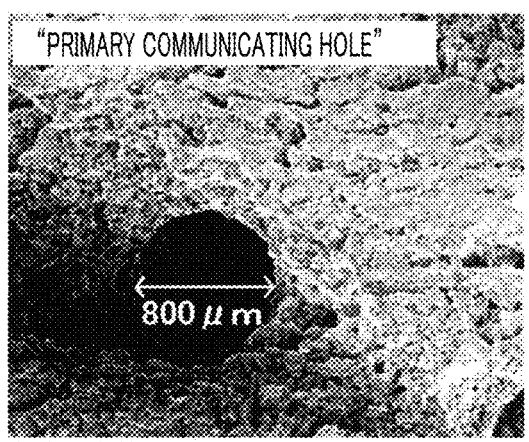
FIG. 31 shows scanning electron microscope (SEM) images of a calcium phosphate molded article having three phases of communicating holes.
Figure 31:
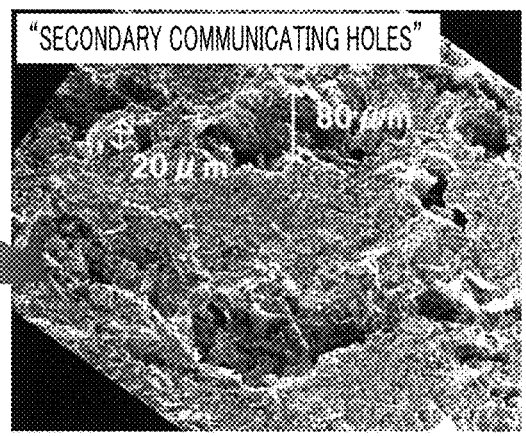
Figure 31:
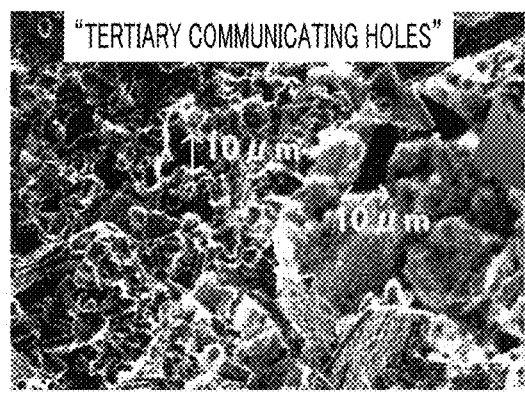

It is preferable that in the internal structure of the calcium phosphate molded article of the invention, communicating holes of about 800 µm (large: also referred to as primary communicating holes), communicating holes of about 20 to about 80 µm (medium: also referred to as secondary communicating holes), and communicating holes of about 1 to 10 µm (small: also referred to as tertiary communicating holes) exist. A schematic diagram of a calcium phosphate molded article having the above-described three phases of communicating holes is shown in FIG. 30, and a SEM image is shown in FIG. 31. The primary communicating holes are formed by the design of a 3D printer, the secondary communicating holes are formed by increasing fluidity while leaving aggregation of powder, and the tertiary communicating holes are formed by voids of the powder. The secondary communicating holes are related to the relatively compact layers and the relatively sparse layers.

Preferably, the calcium phosphate molded article of the invention has peaks and troughs in an alternate manner, in a waveform chart based on a nanofocus X-ray CT image of the calcium phosphate molded article, with the horizontal axis representing the distance in one direction of the molded article and the vertical axis representing the relative CT intensity.

Preferably, the calcium phosphate molded article has at least 5 or more (more preferably at least 7 or more, and even more preferably at least 10 or more) peaks.

The pitch between a first peak and a second peak next to the first peak is preferably 50 to 300 µm, more preferably 60 to 200 µm, and even more preferably 70 to 150 µm.

The usage of the calcium phosphate molded article of the invention is not particularly limited; however, for example, the calcium phosphate molded article can be used as, for example, a scaffold material for regenerative medicine, a manufactured product for regenerative medicine or the like (tissue cultured ex vivo), or a tissue repair material. Preferably, the calcium phosphate molded article can be used as a scaffold material for regenerative medicine or a tissue repair material.

A tissue repair material according to the invention is a material that is to be implanted in the living body and thereby contributes to the formation of a tissue at this implanted site, and the tissue repair material may or may not include cells. Furthermore, the calcium phosphate molded article of the invention may or may not include components that accelerate biological reactions, such as growth factors or drugs. Furthermore, the calcium phosphate molded article of the invention may be used as a mixture with an inorganic material such as hydroxyapatite, or may be used as a composite with the above-mentioned inorganic material. The tissue repair material according to the invention also includes a material that not only contributes to the formation of normal tissue usually existing at the site of implantation, but also accelerates the formation of abnormal tissue including scar tissue and the like.

Specific examples of the tissue repair material are not particularly limited; however, examples include repair materials for cartilage, meniscus, skin, and bone. That is, the calcium phosphate molded article of the invention can be used as a therapeutic agent for the regeneration of cartilage, meniscus, skin, or bone. As long as the regeneration described above is needed, the disease is not limited; however, examples of a disease associated with cartilage deficiency include arthrosis deformans, osteochondral defect, osteochondritis dissecans, traumatic cartilage injury, osteoarthritis, relapsing polychondritis, achondrogenesis, injury of intervertebral disk, and intervertebral disk hernia.

The calcium phosphate molded article of the invention can also be used as a therapeutic agent for bone regeneration by being used in combination with graft cells or an osteoinductive drug. Examples of the osteoinductive drug include BMP (bone morphogenetic protein) and bFGF (basic fibroblast growth factor); however, there are no particular limitations.

Since the calcium phosphate molded article of the invention can be used as a tissue repair material, a method for repairing a tissue and a method for treating a disease associated with tissue damage are also included in the invention. The method for repairing a tissue according to the invention includes applying a tissue repair material, which is the calcium phosphate molded article, to a site where the object tissue has been deleted or injured, and may optionally include other steps. Examples of the other steps include applying graft cells and/or an osteoinductive agent before or after, or simultaneously with, the application of the tissue repair material.

Regarding the method of applying a calcium phosphate molded article to a site where the object tissue has been deleted or injured, incision, injection, arthroscope, endoscope, and the like can be used.

It is preferable that the calcium phosphate molded article of the invention has holes communicating with the external space (primary holes). In a case in which a calcium phosphate molded article having the above-described holes is transplanted into a living body, cells can easily enter the interior of the calcium phosphate molded article. It is more preferable that a hole communicating with the external space penetrates through the interior of the molded article and communicates with the external space at both ends of the hole. The average diameter of the holes communicating with the external space is not particularly limited; however, the average diameter is preferably 200 μm to 2,000 μm.

A hole communicating with the external space (primary hole) implies that the hole is formed in the internal space of the molded article from the surface of one site of the molded article. That is, the internal space of the hole is in communication with the external space.

The phrase "a hole communicating with the external space penetrates through the interior of the molded article and communicates with the external space at both ends of the hole" implies that the hole is formed in the internal space of the molded article from the surface of a certain site of the molded article and communicates with the external space through the surface of another site of the molded article.

It is preferable that the molded article has, for example, secondary holes having a larger average diameter than the primary holes, as holes for injecting cells before transplantation.

The cells and the like injected in through the secondary holes infiltrate into the entirety of the molded article through the primary holes.

The shape of the primary holes and the secondary holes may be any of a circular shape, a square shape, a rectangular shape, a hexagonal shape, an octagonal shape, a cross shape, and an elliptic shape.

In a case in which the molded article is a cube or a cuboid, a primary hole can provide an X-communicating hole, a Y-communicating hole, and a Z-communicating hole, respectively, along the various directions as shown in FIG. 1. The respective communicating holes may or may not intersect with one another. The average diameter of the various communicating holes is preferably in the range of 200 μm to 2,000 μm, and from the viewpoint of the ease of cellular infiltration, the average diameter is more preferably 200 μm to 1,200 μm. The average diameter can be measured using, for example, VHX-D510 manufactured by Keyence Corporation. Regarding the term diameter, in a case in which a hole penetrates through and reaches the outer surface of a molded article, and any two points on the outer circumference of the hole at that time are obtained, the diameter refers to the distance between any two points that give the largest distance between two points. In a case in which the shape of the hole is a circular shape, the distance means the diameter, and in a case in which the shape is a rectangular shape, the diameter means a longer one of the diagonals. Regarding the average diameter, in a case in which the number of holes is 1 to 4, the average diameter refers to a value obtained by dividing the sum of the respective diameters by the number of holes, and in a case in which the number of holes is 5 or greater, the average diameter refers to a value obtained by dividing the sum of four diameters by four.

It is preferable that the number of the primary holes communicating with the external space is larger than the number of secondary holes having a larger average diameter than the primary holes.

The molded article may have any shape such as a cube, a cuboid, a cylinder, a triangular prism, or a cone, as long as the molded article has been molded.

Figure 2:
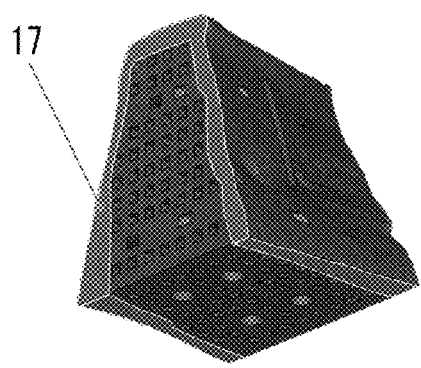
FIG. 2 shows a molded article having a structure reinforcement region.

Regarding the molded article, for example, it is preferable that the thickness of the outer edge portion of the structure that does not have holes is adjusted to 1.3 mm or greater (structure reinforcement region in FIG. 2), so that the molded article can withstand deforming stress in the body after transplantation. The shape of a complicated molded article having various external appearance shape or having primary holes and secondary holes may be established on various three-dimensional CAD software obtained by a computer, and the molded article may be produced as an inherent order-made product or may be produced as a fixed form product having defined form and shape.

[3] Material for Transplantation

The invention provides a material for transplantation comprising a calcium phosphate molded article having a surface partially or entirely coated with a recombinant gelatin.

The calcium phosphate molded article is not particularly limited; however, preferably, a calcium phosphate molded article having the formed described above in the present specification can be used. The ratio of the numbers of atoms of Ca/P of the calcium phosphate used for the material for transplantation is preferably 1.4 to 1.8, more preferably 1.45 to 1.79, and even more preferably 1.50 to 1.70.

The details of the recombinant gelatin are as described above in the present specification. The recombinant gelatin is preferably thermally crosslinked or chemically crosslinked.

The surface of the calcium phosphate molded article coated with a recombinant gelatin preferably exists on the surface and in the interior of the material for transplantation.

In a case in which the surface of the calcium phosphate molded article coated with a recombinant gelatin exists on the surface of the material for transplantation, it is implied that the surface of the material for transplantation is coated with a recombinant gelatin.

In a case in which the surface of the calcium phosphate molded article coated with a recombinant gelatin exists in the interior of the material for transplantation, it is implied that the material for transplantation, that is, the calcium phosphate molded article, is porous, and the surface that forms the holes existing in the interior of the calcium phosphate molded article is coated with a recombinant gelatin.

The calcium phosphate molded article is preferably block-shaped or granular.

A block shape is not limited to a three-dimensional shape composed only of planes, and also includes a curved surface solid having a curved surface. An example of the block shape may be a cuboid shape having a length of 2.0 to 100.0 mm, a width of 2.0 to 100.0 mm, and a height of 2.0 to 100.0 mm.

A granular shape means aggregation of particles having a particle size of about 0.5 to 2.0 mm.

The invention will be explained more specifically by the following Examples; however, the invention is not intended to be limited by the Examples.

EXAMPLES

Example 1

(1) Method for Producing Calcium Phosphate Powder

As raw materials of a calcium phosphate powder, $Ca_4(PO_4)_2O$ (tetracalcium phosphate: TTCP) and $CaHPO_4 \cdot 2H_2O$ (calcium hydrogen phosphate dihydrate: DCPD) were used. The ratio of the numbers of atoms of Ca/P of TTCP is 2.0, and the ratio of the numbers of atoms of Ca/P of DCPD is 1.0. Mixed powders having different ratios of the numbers of atoms of Ca/P as a whole were produced by varying the mixing ratio of TTCP and DCPD. The mixing ratios (molar ratios) of TTCP and DCPD and the ratios of the numbers of atoms of Ca/P of the mixed powders at that time are presented in Table 1.

TABLE 1

| TTCP | DCPD | Ratio of numbers of atoms of Ca/P |
|------|------|-----------------------------------|
| 1.0  | 0.0  | 2.00 |
| 0.9  | 0.1  | 1.95 |
| 0.8  | 0.2  | 1.89 |
| 0.7  | 0.3  | 1.82 |
| 0.65 | 0.35 | 1.79 |
| 0.5  | 0.5  | 1.67 |
| 0.33 | 0.67 | 1.50 |
| 0.25 | 0.75 | 1.40 |
| 0.2  | 0.8  | 1.33 |
| 0.1  | 0.9  | 1.18 |
| 0.0  | 1.0  | 1.00 |

(2) Method for Producing Organic Acid Solution

Solutions having different pH values while having a constant amount of organic acid ions included were produced by adjusting the mixing ratio of an organic acid and sodium salt of the organic acid. Specifically, for example, in the case of citric acid, a solution having a desired pH was produced by mixing a 1 mol/L solution of citric acid and a 1 mol/L solution of trisodium citrate.

(3) Evaluation Method

Onto a calcium phosphate powder produced in the above section (1), the organic acid solution produced in the above section (2) was dropped by jetting. The powder and the organic acid solution were introduced into a Z-Printer 310 Plus (3D Systems Corporation (formerly known as Z Corporation)), and a sample of a cuboid that measured 20×20×5 mm and had five holes having a size of 2×2 mm opened along the thickness direction, was produced. The proportion by volume of the organic acid solution supplied to a unit volume of the powder was set to 42%, and the lamination pitch of the calcium phosphate powder was set to 100 μm. In regard to the production of a molded article using Z-Printer 310 Plus, the molded article as described above is produced by repeating a step of forming a layer containing a calcium phosphate powder on a substrate, and a step of producing a calcium phosphate molded article by jetting an organic acid solution through a nozzle unit into a liquid droplet state and thereby dropping the organic acid solution onto the layer containing a calcium phosphate powder.

The types of the calcium phosphate powder and the organic acid solution are as disclosed in Table 2 and Table 3. The calcium phosphate powder onto which the organic acid solution had been dropped was left to stand for 30 minutes while the temperature was kept at about 40° C., and then removal of the calcium phosphate powder at unnecessary parts (calcium phosphate powder that had not undergone molding by the organic acid solution) was performed using compressed air. The removal of the calcium phosphate powder at unnecessary parts was evaluated according to the following criteria, and the strength of the calcium phosphate powder was evaluated. Rating A implies that the calcium phosphate molded article has sufficient strength.

Rating A: A case in which unnecessary parts could be removed without any problem Rating B: A case in which partial damage occurred in the calcium phosphate powder onto which the organic acid solution had been dropped Rating C: A case in which the calcium phosphate powder onto which the organic acid solution had been dropped disintegrated (4) Results of Evaluation The results of evaluation obtained in the case in which citric acid solutions having different pH values were dropped onto calcium phosphate powders produced by varying the ratio of the numbers of atoms of Ca/P, are presented in Table 2.

TABLE 2

| Ratio of numbers of atoms of Ca/P | pH of citric acid solution | | | |
|---|---|---|---|---|
| of powder | 1.0 | 2.4 | 3.5 | 4.2 |
| 2.0  | B | B | C | C |
| 1.89 | B | B | C | C |
| 1.79 | A | A | A | C |
| 1.67 | A | A | A | C |
| 1.40 | A | A | A | C |
| 1.33 | C | C | C | C |
| 1.18 | C | C | C | C |

The results of evaluation obtained in the case in which pH 3 solutions of various organic acids were dropped onto a calcium phosphate powder having a ratio of the numbers of atoms of Ca/P of 1.67, are presented in Table 3. Acids having lower solubility than malic acid (whose calcium salt has a solubility in water of 0.92 g/100 g) (citric acid, oxalic acid, tartaric acid, and malonic acid) obtained rating A, while succinic acid (solubility 1.27) obtained rating B, and lactic acid, acetic acid, and gluconic acid having higher solubility obtained rating C.

TABLE 3

| | Solubility of calcium salt of organic acid in water (g/100 g) | | | | |
|---|---|---|---|---|---|
| Rating | 0.1 or lower | Higher than 0.1 and 0.5 or lower | Higher than 0.5 and 1.0 or lower | Higher than 1.0 and 1.5 or lower | Higher than 1.5 |
| A | Citric acid Oxalic acid Tartaric acid | Malonic acid | Malic acid | | |
| B | | | | Succinic acid | |
| C | | | | | Lactic acid Acetic acid Gluconic acid |

[Evaluation on Precision and Hardening Rate]

The data of a 3D (three-dimensional)-shaped article with holes that measured 2 mm on each side were used for actual modeling, and the size of the holes of the shaped article was measured. It is considered that measured values are always smaller than design values, and due to bleeding of the organic acid solution, even those parts that are not assumed to undergo hardening at the time of designing may also be hardened. Furthermore, it is considered that bleeding is reduced as the hardening rate becomes faster. Thus, an evaluation was performed based on an index calculated by the formula: (measured value)/(design value)×100, for which an index value of 75% or higher was rated as A; an index value of 50% or higher and lower than 75% was rated as B; an index value of 25% or higher and lower than 50% was rated as C; and a non-measurable case was rated as D. This index implies that as the value is closer to 100%, the design value can be reproduced.

As the result, gluconic acid, which is an acid whose calcium salt has a solubility (g/100 mL) in water of 1.0 or lower, caused sample disintegration, and therefore, measurement could not be achieved. The acid was rated as D.

From the results described above, it was found that in a case in which an organic acid solution having a pH 3.5 or lower and including an organic acid whose calcium salt has a solubility in water of 1 g/100 mL or lower, is jetted out and dropped onto a calcium phosphate powder having a ratio of the numbers of atoms of Ca/P of 1.4 to 1.8, satisfactory evaluation results can be achieved.

<Method for Producing Calcium Phosphate Molded Article>

Regarding an ink, an aqueous solution of sodium citrate adjusted to pH 3.15 was produced by mixing 1.0 mol/L citric acid with 1.0 mol/L trisodium citrate dihydrate at a volume ratio of citric acid:trisodium citrate dihydrate=3:1. This aqueous solution of sodium citrate thus produced was referred to as Na citrate ink.

Regarding a powder, in a case in which the particle size (μm) at the point of cumulative 10% from the finer size side is denoted as d10; the particle size (μm) at the point of cumulative 25% from the finer size side is denoted as d25; the particle size (μm) at the point of cumulative 50% from the finer size side is denoted as d50; the particle size (μm) at the point of cumulative 75% from the finer size side is denoted as d75; and the particle size (μm) at the point of cumulative 90% from the finer size side is denoted as d90, TTCP has a value of d50=7.4 which corresponds to the median diameter, and DCPD has a value of d50=19.5 TTCP and DCPD were mixed such that the final ratio of the numbers of atoms of Ca/P would be 1.5, and more specifically, the two were mixed at a molar ratio of TTCP:DCPD=1:2, or at TTCP:DCPD=219.8 g:206.5 g. This mixture was referred to as the Ca phosphate powder.

The calcium phosphate powder thus mixed had a value of d50=17.0 μm and included particles having a particle size of 5 to 15 μm at a proportion of about 35% by volume, and particles having a particle size of 25 to 100 μm at a proportion of 32% by volume. Measurement was made using LMS-2000e manufactured by Seishin Enterprise Co., Ltd. as a laser diffraction type particle size distribution analyzer, and using ethanol as the dispersing medium.

Figure 3:
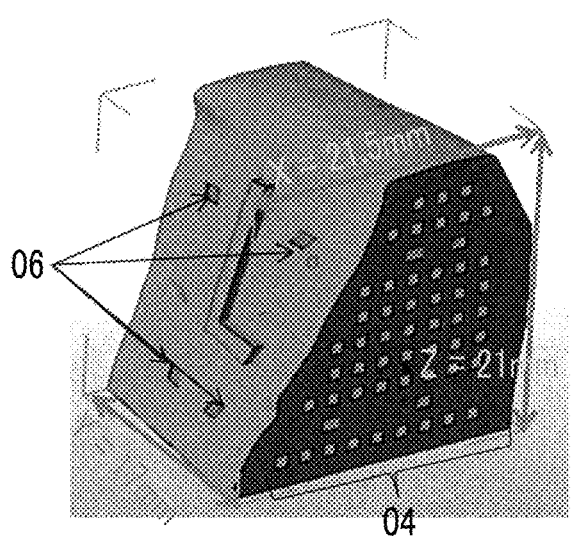
FIG. 3 is a design drawing for the production of a molded article by a 3D printer.
Figure 4:
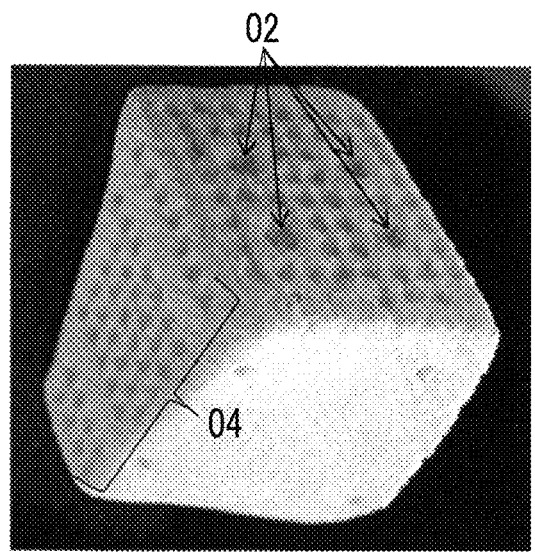
FIG. 4 shows a manufactured molded article.

A molded article was designed as shown in FIG. 3 by using a 3D printer (Z-Printer 310 Plus), replacing the ink and the powder with the Na citrate ink and the Ca phosphate powder, and setting the lamination thickness to 100 μm. The size at this time was set to X=21.5 mm, Y=17 mm, and Z=21 mm. Four secondary holes having a circular shape with a diameter of 2 mm and single-sided penetration were provided, and the non-penetrating ends thereof were positioned at a site 9 mm away from the outer surface. Primary holes were designed such that square-shaped holes having an average diameter of 900 μm would orthogonally intersect one another in the X-, Y-, and Z-directions, and these were designated as X-communicating holes, Y-communicating holes, and Z-communicating holes of the primary holes, respectively. Thus, 64 X-communicating holes, 51 Y-communicating holes, and 51 Z-communicating holes were produced. In order to suture and fix the molded article, suture holes were designed. After the molded article was molded with the 3D printer, the molded article was dried inside the 3D printer at 35° C. for one hour, and any excess powder was removed using compressed air (an air blow stream producing compressed air adjusted to 0.15 MPa using an air gun). This molded article was heated in a muffle furnace by increasing the temperature by 100° C. in one hour each time, and then, the molded article was sintered for 2 hours at 1,100° C. Heating for sintering was turned off, and the molded article was left to stand therein for 8 hours without opening the lid of the muffle furnace. After the muffle furnace reached a temperature lower than or equal to 100° C., the sintered molded article was taken out, and thus the molded article (FIG. 4) was obtained.

<Evaluation>

In order to evaluate permeability into the entire area of the molded article, 10 mL of a mixed liquid obtained by adding a 1.0 mass % dye ink (manufacture by Pilot Corporation, Blue Black for fountain pens, INK-30-BB) to PBS+ (in this case, D8662 manufactured by SIGMA-ALDORICH Corporation was used. PBS is phosphate-buffered physiological saline and is a buffer solution used for experiments in biochemistry and the like. PBS is composed of ions that are universally available in the living body, and the composition includes NaCl, KCl, $Na_2HPO_4$, $KH_2PO_4$, and the like at pH 7.4. PBS+ further includes calcium and magnesium) was used, and permeability into a molded article without holes, permeability into a molded article having secondary holes only, and a permeability having primary holes and secondary holes were investigated.

Permeability was measured as follows. 10 mL of a dye-containing PBS+ solution was introduced into a plastic container having a diameter of 55 mm, and the depth of the solution was adjusted to about 3 mm. A molded article was immersed therein, and measurement was made to find how many seconds it took from immediately after immersion to achieve coloration of the entire area of the molded article. As a result, with regard to the time required for the solution to permeate through the entire area of the molded article, in the molded article without holes, even though one hour or longer passed, coloration of a half or more of the top face was not achieved. Coloration of the entire area of the molded article was observed within 10 minutes in the molded article having secondary holes only, and within 5 seconds in the molded article having primary holes and secondary holes. From these results, it was found that permeability into the molded article was markedly high in the molded article having primary holes and secondary holes.

Example 2

Step of Hardening Molded Article by Immersion

The calcium phosphate powder having a ratio of the numbers of atoms of Ca/P of 1.67, which was produced in section (1) of Example 1, was introduced into Z-Printer 310 Plus (3D Systems Corporation (formerly known as Z Corporation)), and a molded article having a size of 5×5×12 mm was produced using a citric acid solution at pH 3. The proportion by volume of the organic acid solution supplied to a unit volume of the powder was set to 42%, and the lamination pitch of the calcium phosphate powder was set to 100 μm. In regard to the production of a molded article using Z-Printer 310 Plus, a molded article having a size of 5×5×12 mm is produced by repeating a step of forming a layer containing a calcium phosphate powder on a substrate and a step of producing a calcium phosphate molded article by jetting a citric acid solution through a nozzle unit into a liquid droplet state and dropping the citric acid solution onto the layer containing a calcium phosphate powder.

A molded article produced as described above was immersed in any one of the following solution A, solution B, and solution C for 12 hours, and the compressive strength before and after immersion was measured.

Solution A: 0.5 mol/L solution of sodium dihydrogen phosphate (pH 4.3)

Solution B: 0.5 mol/L solution of disodium hydrogen phosphate (pH 9)

Solution C: 1:1 mixed solution of solution A and solution B (pH 6.6)

Measurement of the compressive strength was carried out using ELECTROFORCE 5500 of TA Instruments, Inc. The compressive strength (MPa) was determined by applying a load in the longitudinal direction of a sample having a size of 5×5×12 mm at a rate of 0.17 mm/second, and dividing the maximum load (N) at the time of sample breakage by the cross-sectional area.

The compressive strength, which was 2.2 MPa before immersion, became 4.2 MPa in the case in which the sample was immersed in solution A; became 3.5 MPa in the case in which the sample was immersed in solution B; and became 3.9 MPa in the case in which the sample was immersed in solution C. It was confirmed that hardening of the molded article proceeded as the result of immersing the molded article into the solution, and thus strength increased.

Example 3

Step of Hardening Molded Article by Heating

A calcium phosphate molded article produced in the same manner as in Example 2 was heated for 4 hours at 1,100° C. or 1,200° C. using a muffle furnace. The compressive strength before and after heating was measured in the same manner as in Example 2. The compressive strength, which was 2.2 MPa before heating, became 3.5 MPa in the case of heating the molded article at 1,100° C.; and became 6.1 MPa in the case of heating the molded article at 1,200° C. It was confirmed that strength was increased by heating of the molded article. Furthermore, the organic acid used for modeling could also be removed by thermal decomposition.

Example 4

Verification of Effect of RCP Modification in Cellular Adhesiveness (Operation 1) Bone prosthetic material, OSFERION (manufactured by Olympus Terumo Biomaterials Corporation), as β-TCP particles was immersed, with shaking, in a 7.5% solution of (RCP comprising an amino acid sequence set forth in SEQ ID NO:1) for 3 hours at 37° C. Subsequently, the molded article was dried for 12 hours at 50° C. The molded article was subjected to a thermal crosslinking treatment for 20 hours at 160° C., and thus a preparation was obtained.

(Operation 2) The preparation thus produced was placed on a 24-well ultralow adhesion plate (manufactured by Corning, Inc.) in an amount of 10 mg/well, and cells (NIH-3T3) were inoculated thereon at a rate of 50,000 cells/well.

(Operation 3) In 24 hours after the inoculation, the cells were stained by calcein staining, and then fluorescence observation and observation with a scanning electron microscope (SEM) were carried out.

Comparative Example 4

An example obtained by performing operations in the same manner as in Example 4, except that Operation 1 was not carried out, was designated as Comparative Example 4.

Figure 5:
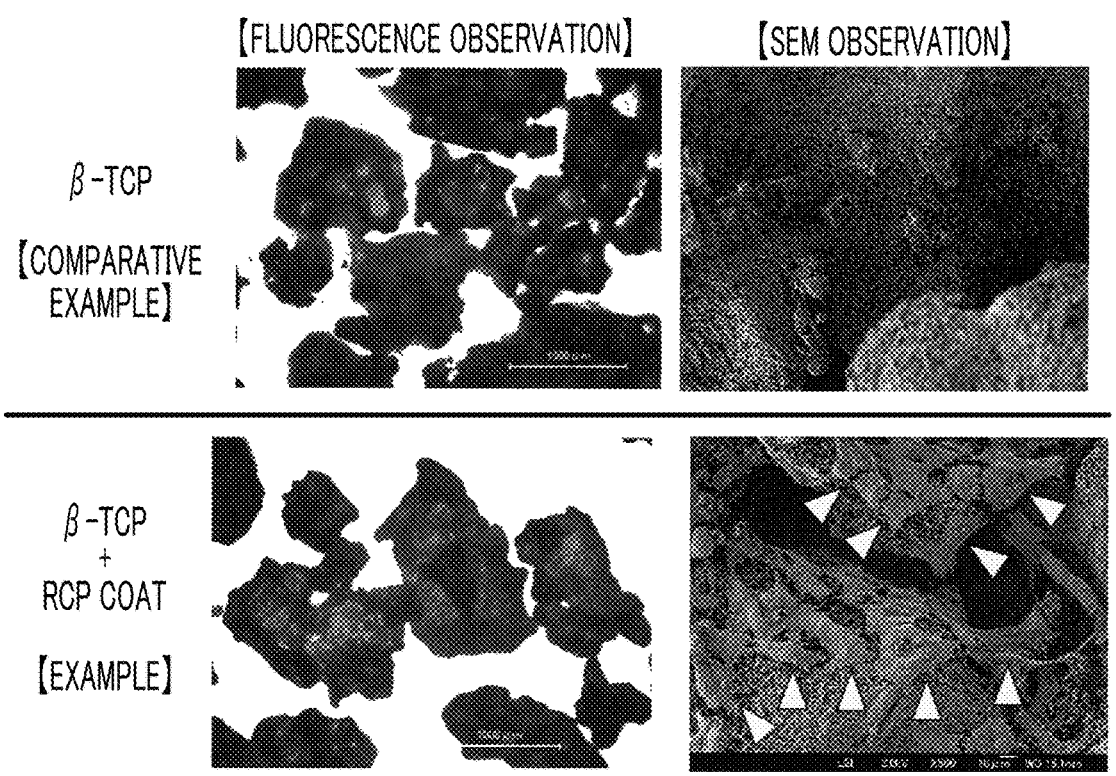
FIG. 5 shows the results of confirming a recombinant gelatin modification effect (cellular adhesiveness) on β-TCP particles.

The results of Example 4 and Comparative Example 4 are shown in FIG. 5. In Example 4, an enhancement of cellular adhesiveness was recognized, compared to Comparative Example 4 (FIG. 5).

Example 5

Confirmation of RCP Modification Effect by Bone Regeneration Induction Test in Rat Parietal Bone-Defective Part SD rats (male, 10 to 12 weeks old, 0.3 to 0.5 kg) were used as experimental animals, and the parietal bones of the rats were exposed to produce circular-shaped bone-defective parts having a diameter of 5 mm. Each of the bone-defective parts was filled with about 10 mg of the preparation of Example 4, and then the skin was sutured.

In the eighth week after the enthesis, the rats were brought to death by exsanguinations, and the head portions were extracted. The parietal bones including the embedded parts were subjected to a histological observation by HE staining.

Comparative Example 5

An example obtained by performing operations in the same manner as in Example 5, except that the preparation of Comparative Example 4 was used instead of the preparation of Example 4, was designated as Comparative Example 5.

Figure 6:
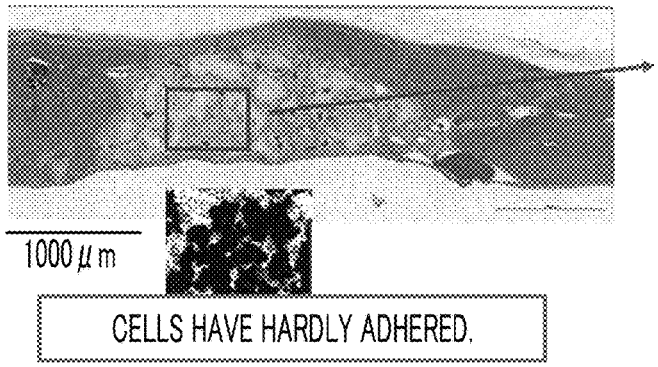
FIG. 6 shows the results of confirming a recombinant gelatin modification effect (osteogenesis) on β-TCP particles.
Figure 6:
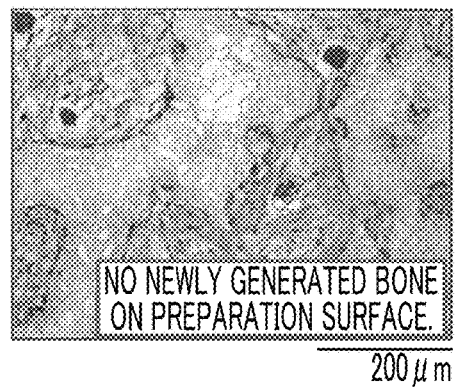
Figure 6:
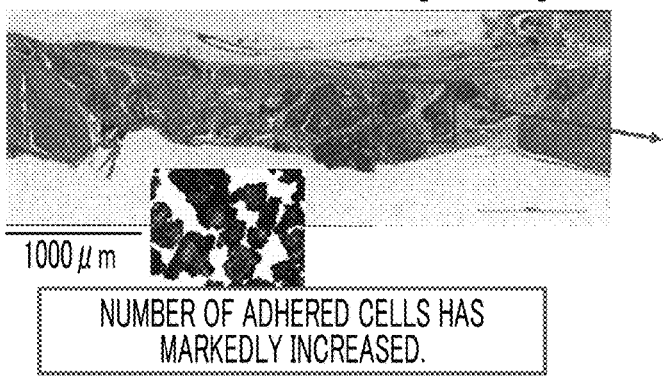
Figure 6:
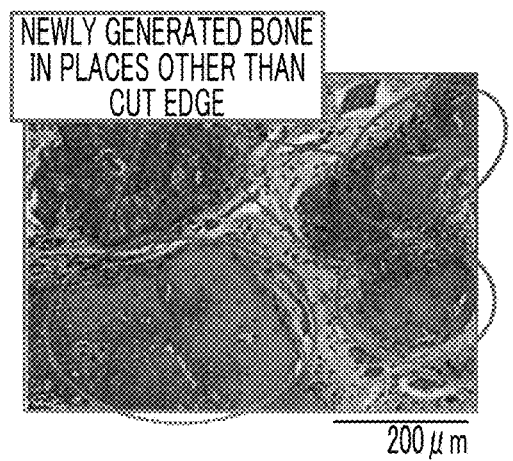

The results of Example 5 and Comparative Example 5 are presented in FIG. 6. In Example 5, an enhancement of osteogenesis was recognized, compared to Comparative Example 5 (FIG. 6).

Example 6

Porosity, Specific Gravity, and Water Absorption Infiltration Rate of Calcium Phosphate Molded Article A calcium phosphate molded article was produced as follows.

<Method for Producing Calcium Phosphate Molded Article>

Regarding an ink, an aqueous solution of sodium citrate adjusted to pH 3.15 was produced by mixing 1.2 mol/L citric acid with 1.2 mol/L trisodium citrate dihydrate at a volume ratio of citric acid:trisodium citrate dihydrate=3:1. This aqueous solution of sodium citrate thus produced was referred to as Na citrate ink.

Regarding a powder, in a case in which the particle size (μm) at the point of cumulative 10% from the finer size side was denoted as d10; the particle size (μm) at the point of cumulative 25% from the finer size side was denoted as d25; the particle size (μm) at the point of cumulative 50% from the finer size side was denoted as d50; the particle size (μm) at the point of cumulative 75% from the finer size side was denoted as d75; and the particle size (μm) at the point of cumulative 90% from the finer size side was denoted as d90, a TTCP powder having a d50 of 7.4 μm, which corresponds to the median diameter, and a DCPD powder having a d50 of 19.5 μm were prepared. The powders were mixed such that the final ratio of the numbers of atoms of Ca/P would be 1.5. More specifically, the TTCP powder and the DCPD powder were mixed at a molar ratio of TTCP:DCPD=1:2, or at TTCP:DCPD=219.8 g:206.5 g. This mixture was referred to as Ca phosphate powder.

The Ca phosphate powder thus mixed included particles having a particle size of 5 to 15 μm at a proportion of about 35% by volume and particles having a particle size of 25 to 100 μm at a proportion of 32% by volume. Measurement was made using LMS-2000e manufactured by Seishin Enterprise Co., Ltd. as a laser diffraction type particle size distribution analyzer, and using ethanol as the dispersing medium.

A 3D printer (Z-Printer 310 Plus) was used, the ink and the powder were replaced with the Na citrate ink and the Ca phosphate powder, and the lamination thickness was set to 100 μm.

The structure was cylindrical in shape, and while assuming that sintering would result in 10% shrinkage, the structure was shaped to have a diameter of ϕ8.8 mm and a height of 22 mm.

After a molded article was molded with the 3D printer, the molded article was dried inside the 3D printer at 35° C. for one hour, and any excess powder was removed using compressed air (an air blow stream producing compressed air adjusted to 0.15 MPa using an air gun). This molded article was heated in a muffle furnace by increasing the temperature by 100° C. in one hour each time, and then, the molded article was sintered for 2 hours at 1,100° C. Heating for sintering was turned off, and the molded article was left to stand therein for 8 hours without opening the lid of the muffle furnace. After the muffle furnace reached a temperature lower than or equal to 100° C., the sintered molded article was taken out, and thus a cylindrical molded article having a diameter of ϕ8 mm and a height of 20 mm was obtained.

For the calcium phosphate molded article produced as described above and commercially available products (three types as described below), the porosity, specific gravity, and water absorption infiltration rate were measured by the following methods.

SUPERPORE (manufactured by Pentax Corporation) Product No. KB-6-1, diameter 8×length 20 mm SUPERPORE (manufactured by Pentax Corporation) Product No. HB-50-0820, diameter 8×length 20 mm SUPERPORE EX (manufactured by Pentax Corporation) Product No. XC-0820, diameter 8×L 20 mm The three types of SUPERPORE described above are white porous materials formed from p-type tricalcium phosphate.

<Method for Measuring Porosity>

The porosity was measured by a mercury intrusion method. A mercury intrusion method is a method of applying pressure in order to cause mercury to infiltrate into pores of a powder by utilizing the fact that mercury has high surface tension, and determining the specific surface area or the pore distribution from the pressure and the amount of intruded mercury. Porosity was measured using POREMASTER 60GT (manufactured by Quantachrome Corporation). Measurement was made under the following standard conditions.

Hg Surface Tension 480.00 erg/cm$^2$

Hg Contact Angle (I) 141.30°, (E) 141.30°

Temperature 20.00 [° C.]

Regarding the sample size, the sample was a cylindrical shape having a diameter of 0.462 mm and a height of 0.959 mm.

<Measurement of Specific Gravity>

The weight of the calcium phosphate molded article produced as described above was measured with an electronic balance that was capable of measuring up to $1/1000$ g, and the diameter and the height were measured using vernier calipers that were capable of measuring up to $1/100$ mm so as to determine the volume. Next, the specific gravity was determined by dividing the weight by the volume.

<Method for Measuring Water Absorption Infiltration Rate>

An experiment system for determining the water absorption infiltration rate was established.

The temperature in the laboratory was adjusted to 23° C., the humidity was adjusted to 30%, and experiment and measurement were carried out. As a fountain pen ink, INK-30-BB manufactured by Pilot Corporation was used.

Figure 7:
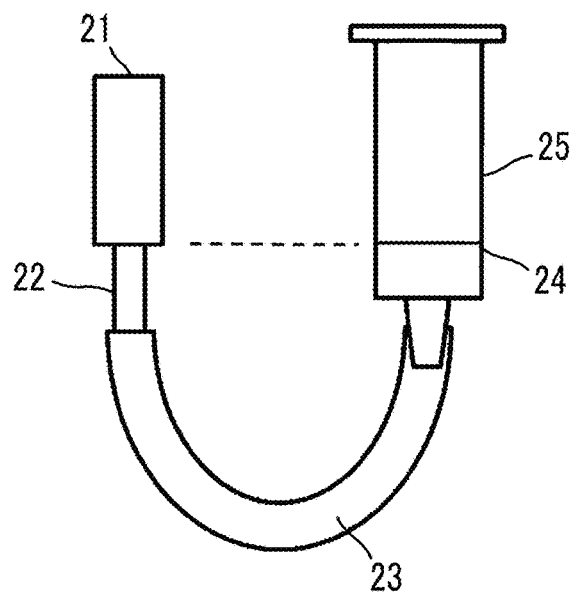
FIG. 7 shows an experiment system used for the measurement of the water absorption infiltration rate.

An experiment system shown in FIG. 7 was established using a plastic cylinder having an inner diameter of 2 mm, a tube, and a syringe. A meniscus surface was made at the bottom face of the structure, and the ink was caused to permeate therethrough. The meniscus height was adjusted manually by visual inspection. A calcium phosphate molded article 21 was produced to have a size of 8 mm in diameter× 20 mm in height. The inner diameter of the plastic cylinder 22 was 2 mm. The length of the tube 23 was 100 mm. The liquid level 24 was adjusted to be equal to the height at which the plastic cylinder 22 and the calcium phosphate molded article 21 were contacted, from the initiation to completion of water absorption infiltration. As the syringe 25, a 10-mL syringe was used. The inner diameter was made larger than the calcium phosphate molded article 21.

In the experiment system shown in FIG. 7, as described above, the ink in the syringe was subjected to absorption and infiltration into the calcium phosphate molded article under the conditions in which the height at which the calcium phosphate molded article was contacted with the plastic cylinder, and the height of the level of the ink in the syringe were adjusted to be maintained equal from the initiation to the completion of water absorption and infiltration. In a case in which the height of the region infiltrated by the ink in the calcium phosphate molded article reaches 15 mm within 5 minutes, a value obtained by dividing 15 mm by the time required for infiltration is defined as the water absorption infiltration rate; and in a case in which the height of the region infiltrated by the ink in the calcium phosphate molded article does not reach 15 mm within 5 minutes, a value obtained by dividing the height of the region infiltrated by the ink in the calcium phosphate molded article at the time point of 5 minutes, by 5 minutes, which is the time required for infiltration, is defined as the water absorption infiltration rate.

The measurement results for the porosity, specific gravity, and water absorption infiltration rate are shown in the following table.

TABLE 4

|  | Porosity (%) | Specific gravity (g/ml) | Water absorption infiltration rate (mm/second) |
| --- | --- | --- | --- |
| Calcium phosphate molded article (X-direction: drawing direction) | 64.6 | 0.922 | 1.002 |
| Calcium phosphate molded article (Y-direction: recoat scanning direction) | 64.6 | 0.922 | 0.986 |
| Calcium phosphate molded article (Z-direction: lamination direction) | 64.6 | 0.922 | 0.576 |
| SUPERPORE Product No. KB-6-1 | 75 | 0.757 | 0.010 |
| SUPERPORE Product No. HB-50-0820 | 67 | 1.022 | 0.003 |
| SUPERPORE Product No. XC-0820 | 57 | 1.269 | 0.015 |

Example 7

Sparse-Compact Laminated Structure of Calcium Phosphate Molded Article

<Method for Producing Calcium Phosphate Molded Article>

Regarding an ink, an aqueous solution of sodium citrate adjusted to pH 3.15 was produced by mixing 1.2 mol/L of citric acid and 1.2 mol/L of trisodium citrate dihydrate at a volume ratio of citric acid:trisodium citrate dihydrate=3:1. This aqueous solution of sodium citrate thus produced was referred to as Na citrate ink.

Regarding powders, a TTCP powder having a median diameter (hereinafter, described as d50) of 7.4 μm and a DCPD powder having a d50 of 19.5 μm were prepared, and the powders were mixed such that the final ratio of the numbers of atoms of Ca/P would be 1.5.

More specifically, the TTCP powder and the DCPD powder were mixed at a molar ratio of TTCP:DCPD=1:2, or at a ratio of TTCP:DCPD=219.8 g:206.5 g. This mixture was referred to as Ca phosphate powder. The Ca phosphate powder thus mixed included particles having a particle size of 5 to 15 μm at a proportion of about 35% by volume and particles having a particle size of 25 to 100 μm at a proportion of 32% by volume.

A 3D printer (Z-Printer 310 Plus) was used, the ink and the powder were replaced with the Na citrate ink and the Ca phosphate powder, and the lamination thickness was set to 100 μm.

The structure was a structure obtained by stacking three discs, and the largest disc was a disc having a diameter of 14.4 mm and an overall height of 7.8 mm.

After the molded article was molded with the 3D printer, the molded article was dried inside the 3D printer at 35° C. for one hour, and any excess powder was removed using compressed air (an air blow stream producing compressed air adjusted to 0.15 MPa using an air gun). This molded article was heated in a muffle furnace by increasing the temperature by 100° C. in one hour each time, and then, the molded article was sintered for 2 hours at 1,100° C. Heating for sintering was turned off, and the molded article was left to stand therein for 8 hours without opening the lid of the muffle furnace. After the muffle furnace reached a temperature lower than or equal to 100° C., the sintered molded article was taken out, and thus the molded article was obtained.

<Nanofocus X-ray CT Analysis>

Figure 8:
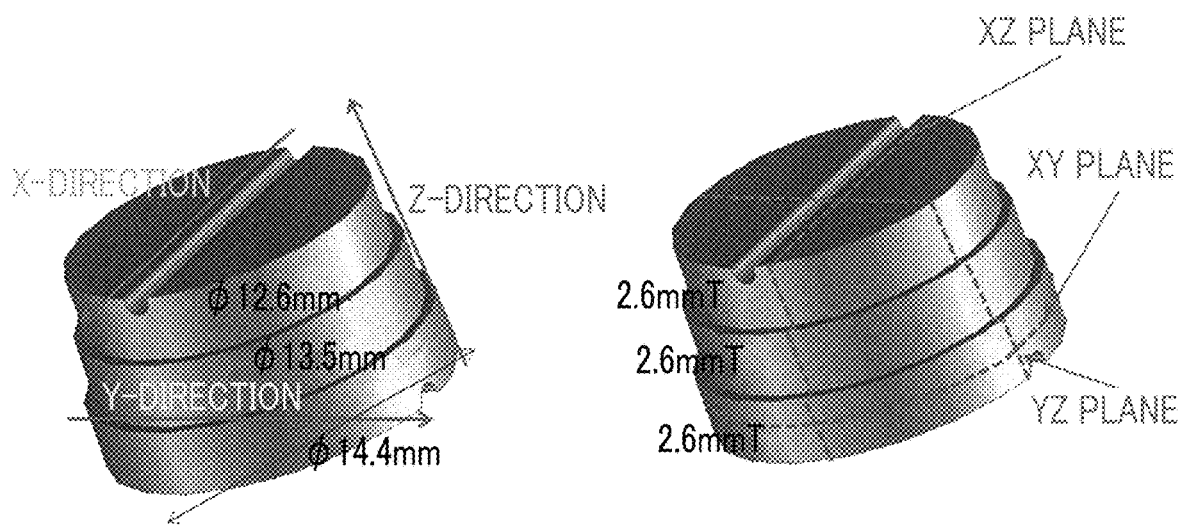
FIG. 8 shows the structure of an object used for an analysis of a sparse-compact laminated structure.

The structure of an object used for an analysis of a sparse-compact laminated structure is shown in FIG. 8.

Observation and analysis were carried out under the following measurement conditions by using PHOENIX NANOTOM M manufactured by General Electronics, Ltd.

Figure 9:
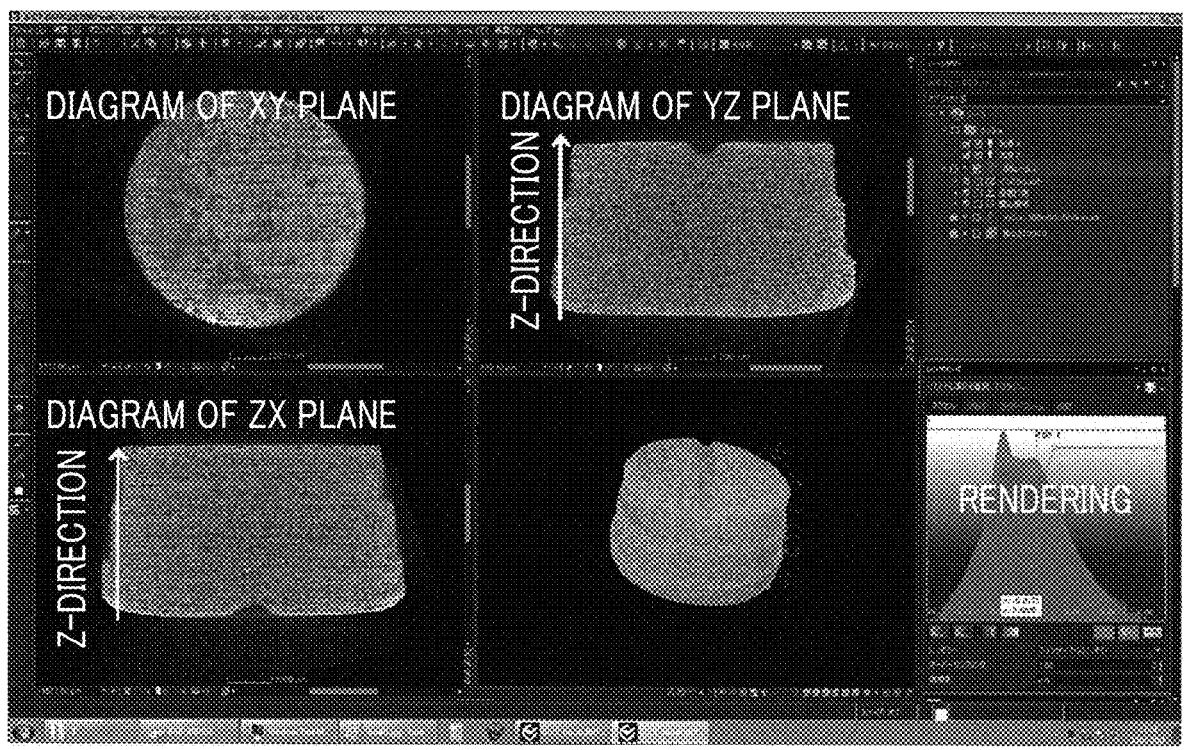
FIG. 9 shows the results of adjusting the way of viewing in a nanofocus X-ray CT analysis such that a compact layer (relatively compact layer) and a sparse layer (relatively sparse layer) can be recognized.

Tube voltage: 120 kV
Tube current: 90 μA
Distance from X-ray source to detector (FDD): 600 mm
Distance from X-ray source to center of rotation of object sample (FOD): 400 mm
Resolution: 6.66 μm in all of X-axis, Y-axis, and Z-axis After measurement was made under the conditions as described above, the way of viewing white, gray, and black was adjusted using VGSTUDIO MAX 3.0.3 64 bit, a software program linked to the apparatus, by which CT images can be analyzed, so that the pattern of the internal structure of the calcium phosphate molded article would be seen, and that compact layers (relatively compact layers) and sparse layers (relatively sparse layers) could be recognized (FIG. 9).

Adjustment of the way of viewing white, gray, and black is as shown in the screen for rendering function in the lower right corner of FIG. 9. It is implied that as the image is displayed brighter, the density of the material becomes relatively higher, and as the image is displayed darker, the density of the material becomes relatively lower. In this case, a brighter image implies a larger amount of calcium phosphate, and a darker image implies a smaller amount of calcium phosphate, approaching the state of voids.

The XY plane, YZ plane, and ZX plane, which geometrically orthogonally intersect one another, are displayed in regions in the screen of VGSTUDIO MAX 3.0.3 64 bit as a diagram of the XY plane, a diagram of the YZ plane, and a diagram of the ZX plane, respectively in FIG. 9.

In the diagram of the YZ plane and the diagram of the XZ plane in the screen, the screen of rendering function is adjusted so that a stripe pattern of white and black is seen. Furthermore, the directions of the calcium phosphate molded article in VGSTUDIO MAX 3.0.3 64 bit are adjusted so that the stripe patterns of white and black in the diagram of the YZ plane and the diagram of the XZ plane face the same direction, and that the intervals between a white stripe and another white stripe coincide as far as possible. Through this operation, sparse layers and compact layers of the sparse-compact laminated structure of the calcium phosphate molded article become parallel to the XY plane.

As shown in FIG. 9, the directions of the calcium phosphate molded article are adjusted, and a direction orthogonally intersecting the stripe pattern of white and black is designated as the Z-axis of the calcium phosphate molded article.

The diagram of the ZX plane including the Z-axis is stored in the computer in the TIFF format, and in the biological imaging field, the TIFF image data are opened using ImageJ 1.50i (ImageJ is an open source image processing software in the public domain developed by the National Institutes of Health (NIH) of the USA), which is a de facto standard image analysis.

Figure 10:
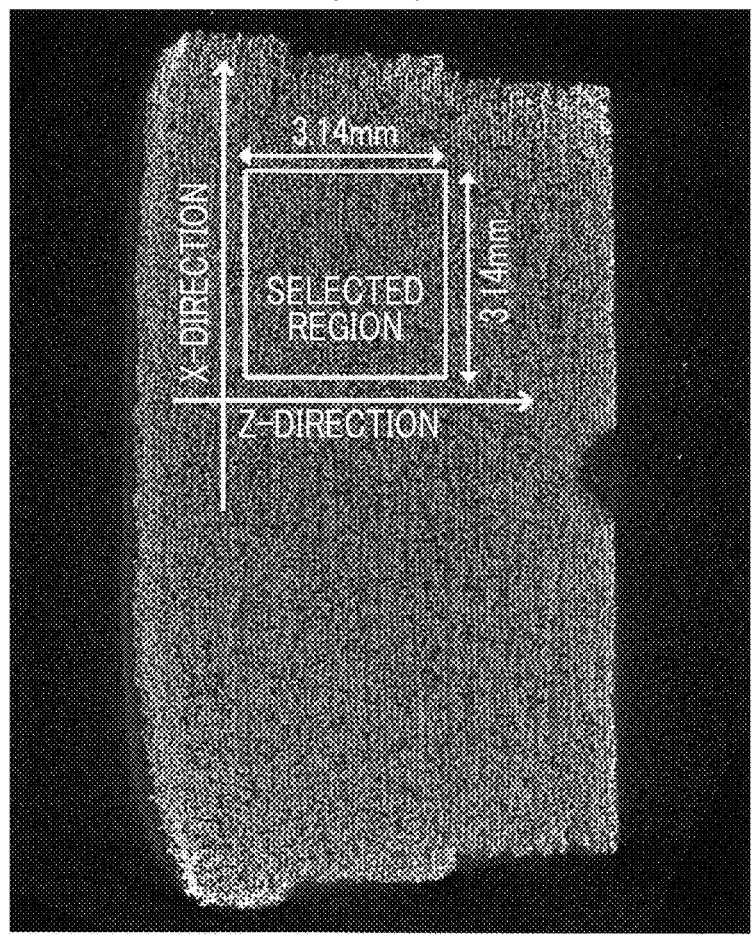
FIG. 10 shows the state in which a region measuring 3.14 mm in the Z-axis direction and 3.14 mm in the X-axis direction is selected in a nanofocus X-ray CT analysis.

In ImageJ 1.50i, a region that measures 3.14 mm in the Z-axis direction and 3.14 mm in the X-axis direction is selected (FIG. 10). In the image of the ZX plane, compact layers and sparse layers are alternately arranged so as to transverse in the Z-direction, and in the X-direction, compact layers extend almost linearly, while sparse layers extend almost linearly.

In a case in which a region in the Z-axis direction is selected, a distance range of from 0.5 mm to 5.0 mm in the Z-axis direction is preferred, and a distance of from 2.0 mm to 4.0 mm is more preferred.

It is preferable to select a region wider than a region of 2.0 mm or more because the region ends without being affected by the locality of the calcium phosphate molded article; however, in a case in which the calcium phosphate molded article is small, the selection cannot be implemented, and therefore, the region is appropriately adjusted. If the region is too large, the subsequent operation becomes enormous. Therefore, the upper limit is set to 5.0 mm, and a distance of up to 4.0 mm is more preferred.

Figure 11:
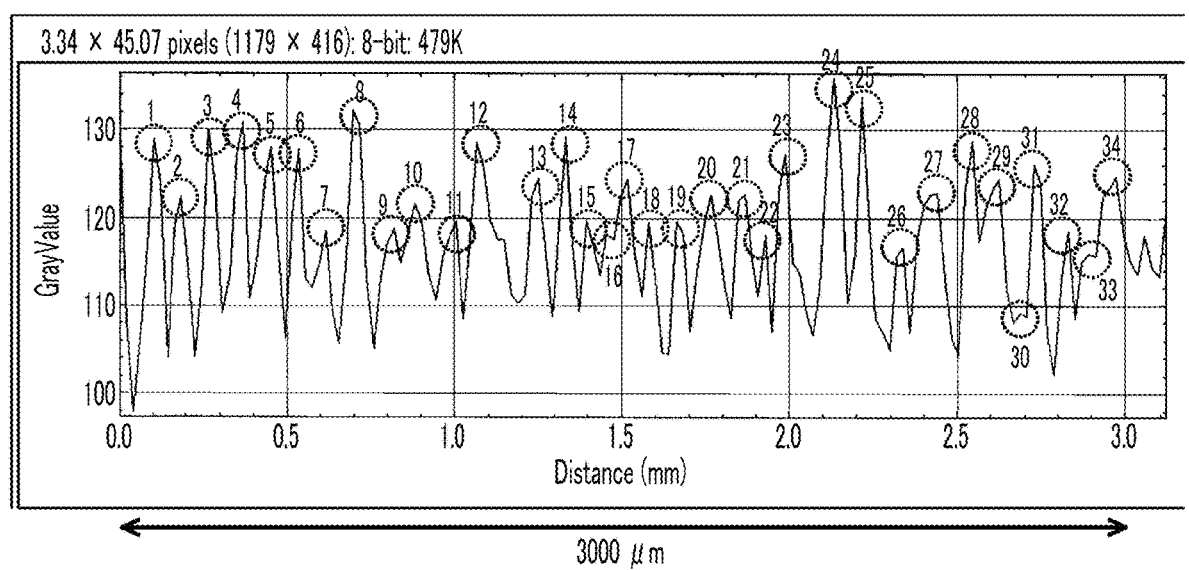
FIG. 11 shows conversion of the region selected in FIG. 10 into a waveform in accordance with the degree of monochromaticity.

Based on the plot profiling function of Imagej 1.50i, the image can be displayed as a waveform, with the horizontal axis representing the distance in the Z-axis direction of the selected region and the vertical axis representing the degree of monochromaticity of the selected region as Gray Value (FIG. 11).

The Gray Value displayed is a value obtained by averaging the Gray Values of various pixels within 3.14 mm on the X-axis in accordance with the distance on the Z-axis. In this case, there are 153 pixels in the distance of 3.14 mm.

At the time of selecting a region in the X-axis direction, a distance range of from 0.5 mm to 5.0 mm in the X-axis direction is preferred, and a distance of from 2.0 mm to 4.0 mm is more preferred.

It is preferable to select a region wider than a region of 2.0 mm or more because the region ends without being affected by the locality of the calcium phosphate molded article and without being affected by the resolution of pixels; however, in a case in which the calcium phosphate molded article is small, the selection cannot be implemented, and therefore, the region is appropriately adjusted. If the region is too large, there is the influence of coincidence of the directions of the sparse layers and compact layers of the calcium phosphate molded article and the X-axis, Y-axis, and Z-axis directions that are established in the VGSTUDIO MAX 3.0.3 64 bit. Therefore, the upper limit is set to 5.0 mm, and a distance of up to 4.0 mm is more preferred.

From the waveform thus obtained, the number of layers and the pitch of a relatively compact layer and a relatively sparse layer are analyzed.

The number of apexes of the compact layers is counted. The apex of a compact layer lies at a site where the substance density becomes relatively higher than the surroundings, and where the coefficient of gradient of the waveform changes from positivity to negativity. The apex of a sparse layer lies at a site where the substance density becomes relatively lower than the surroundings, and where the coefficient of gradient of the waveform changes from negativity to positivity.

In the present case, the selected distance on the Z-axis was 3.14 mm, and thirty-four apexes of compact layers existed in the distance of 3.0 mm in the waveform graph formed by the plot profiling function.

(Distance on the Z-axis/Number of apexes of compact layers) is designated as the pitch in the ZX plane of the sparse-compact laminated structure of the calcium phosphate molded article. In the present case, the value is 3.0 mm/34 apexes, and the pitch is 88.2 μm (FIG. 11).

Figure 12:
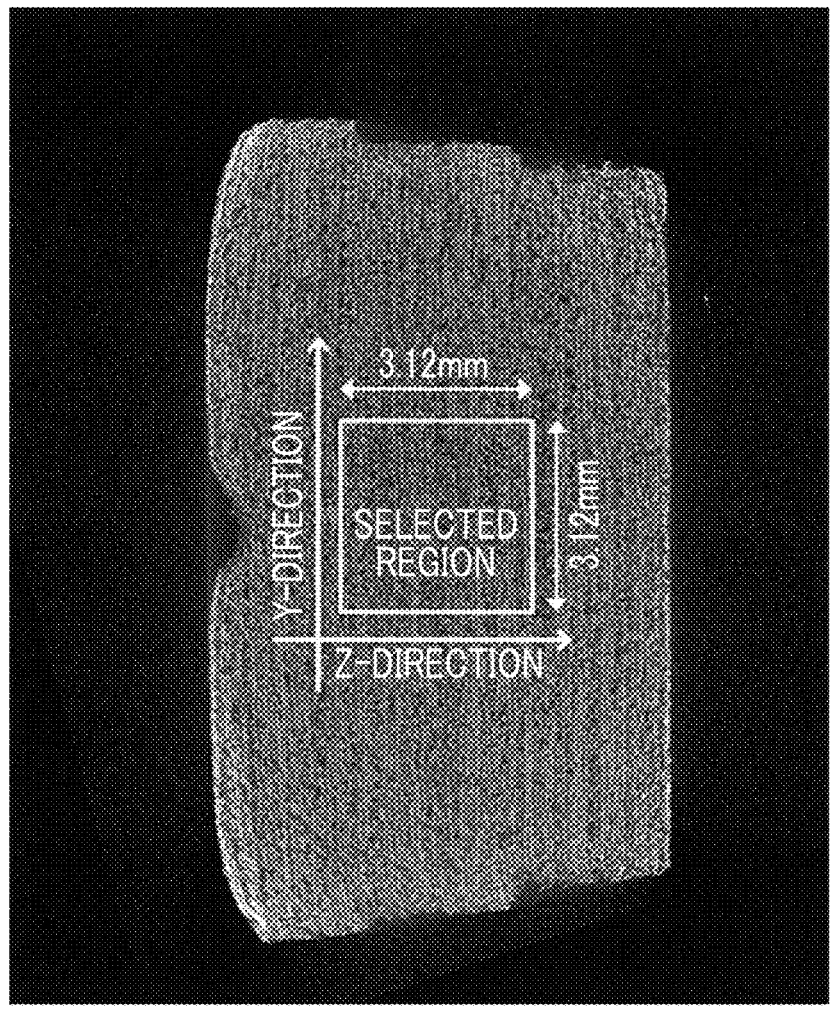
FIG. 12 shows the state in which a region measuring 3.12 mm in the Z-axis direction and 3.12 mm in the Y-axis direction is selected in a nanofocus X-ray CT analysis.

Also from the diagram of the YZ plane (FIG. 12), the pitch in the YZ plane of the sparse-compact laminated structure of the calcium phosphate molded article (FIG. 12) was induced by a processing similar to the diagram of the XZ plane.

Figure 13:
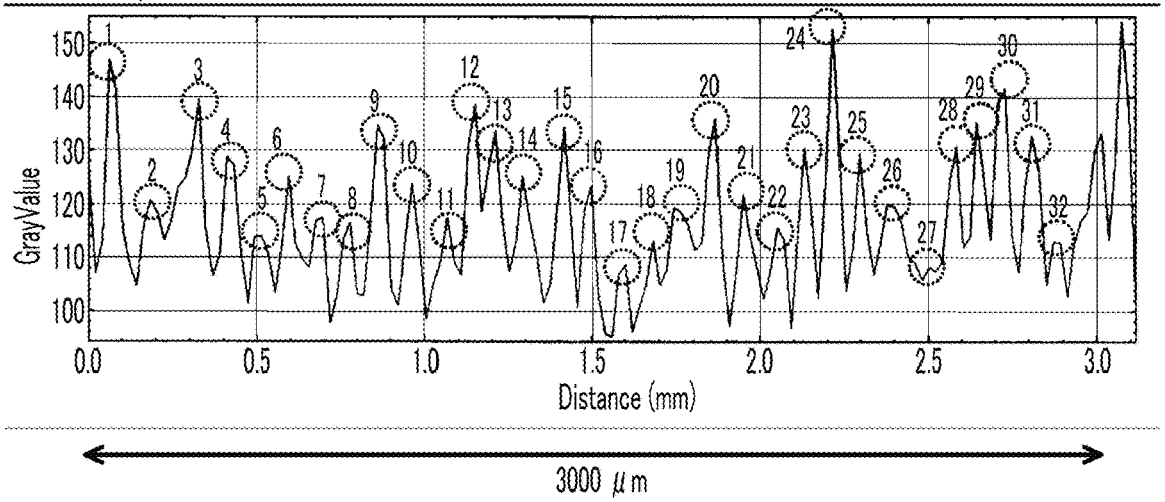
FIG. 13 shows conversion of the region selected in FIG. 12 into a waveform in accordance with the degree of monochromaticity.

(Distance on the Z-axis/Number of apexes of compact layers) is designated as the pitch in the YZ plane of the sparse-compact laminated structure of the calcium phosphate molded article. In the present case, the value is 3.0 mm/32 apexes, and the pitch is 93.8 μm (FIG. 13).

The average of the pitch in the ZX plane of the sparse-compact laminated structure of the calcium phosphate molded article and the pitch in the YZ plane of the sparse-compact laminated structure of the calcium phosphate molded article is designated as the pitch of the sparse-compact laminated structure of the calcium phosphate molded article. In the present case, h(88.2 μm+93.8 μm)/2=90.3 μm is the pitch of the sparse-compact laminated structure of the calcium phosphate molded article.

It is considered that there is a relation between a rapid water absorption infiltration rate of the calcium phosphate molded article and the sparse-compact laminated structure. At the time of measuring the water absorption infiltration rates in the X-direction and the Y-direction, the state of infiltrating through sparse layers that are parallel to the XY plane can be recognized by observing the external appearance of the calcium phosphate molded article by visual inspection or with a magnifying glass. Also, even at the time of measuring the water absorption infiltration rates in the Z-direction, the state of infiltrating in the Z-direction for each layer at the sparse layers and the compact layers, which orthogonally intersect with the Z-direction, while the rate is increased in the sparse layers and is decreased in the compact layers, can be seen.

It is considered to be because, since the voids in the sparse layers range from several millimeters (mm) to several ten millimeters (mm), the voids are not in a bent three-dimensional connection but in a simple, straight, planar connection, and the voids are open on both sides from one surface of the calcium phosphate molded article to the other opposite surface, the infiltrated ink infiltrates without being affected by the resistance of air.

Example 8

Laser Diffraction Type Particle Size Distribution Analysis of Calcium Phosphate Powder The particle size distribution was analyzed using $Ca_4(PO_4)_2O$ (tetracalcium phosphate; TTCP), $CaHPO_4 \cdot 2H_2O$ (calcium hydrogen phosphate dihydrate; DCPD), and a mixed powder of TTCP and DCPD (ratio of the numbers of atoms of Ca/P is 1.5) as calcium phosphate powders, by using the following method and conditions.

Apparatus: LMS-2000e manufactured by Seishin Enterprise Co., Ltd.

Principle of measurement: Particles dispersed in a dispersing medium such as water or ethanol are irradiated with laser light, the angle dependency of the scattered light intensity from the particles is measured, and thereby the particle size distribution of the particles included in the sample is determined.

Measurement range: 0.02 to 2,000
Laser light source: Helium-neon laser
Dispersing medium: Ethanol
Measurement method: Blank measurement is performed using the dispersing medium only, subsequently a sample is dispersed by ultrasonic dispersion for one minute, the sample that has been ultrasonically dispersed is introduced into a dispersing tank, and a particle size distribution analysis is performed in a circulation mode.

Particle Size Distribution: Indicated on a Volume Basis

Figure 14:
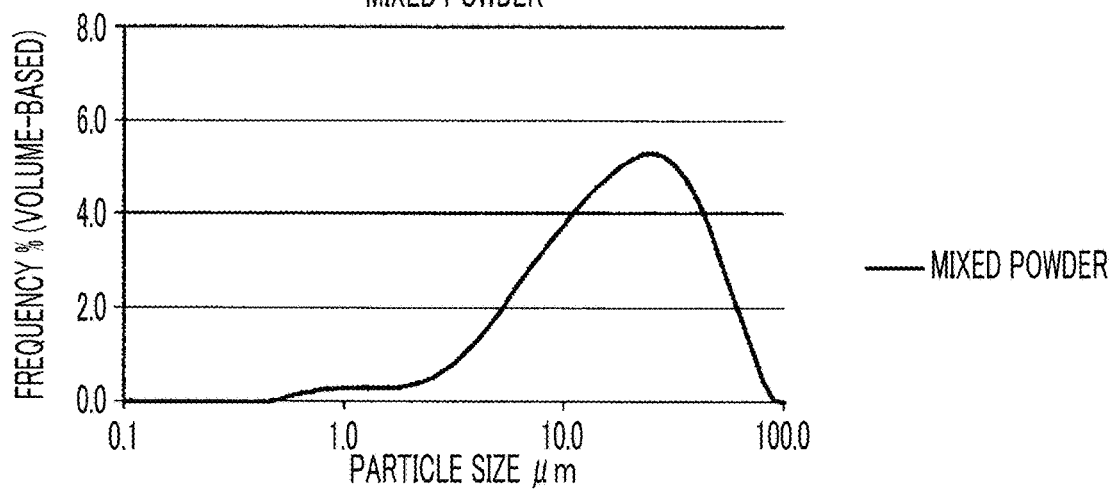
FIG. 14 shows the results of measuring a particle size distribution of a mixed powder.
Figure 15:
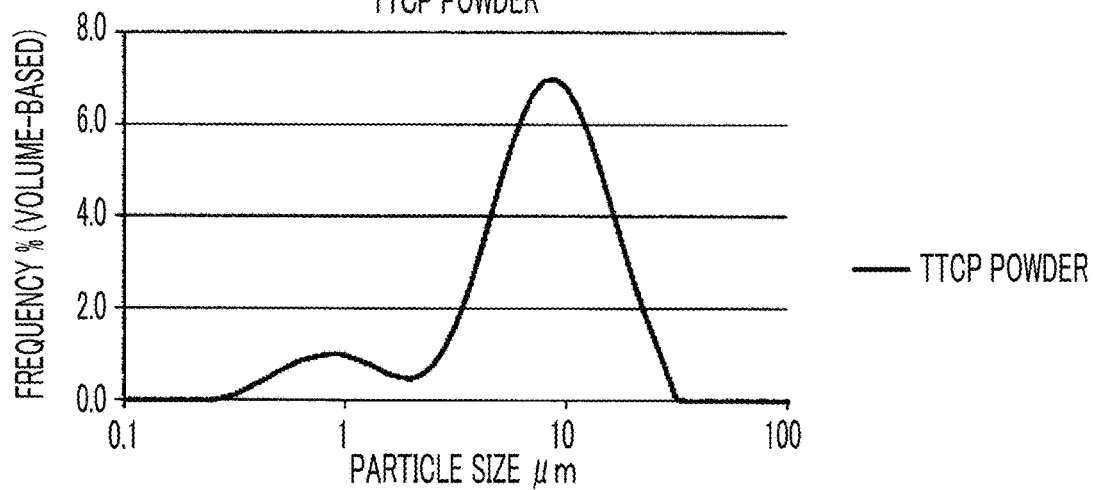
FIG. 15 shows the results of measuring a particle size distribution of a TTCP powder.
Figure 16:
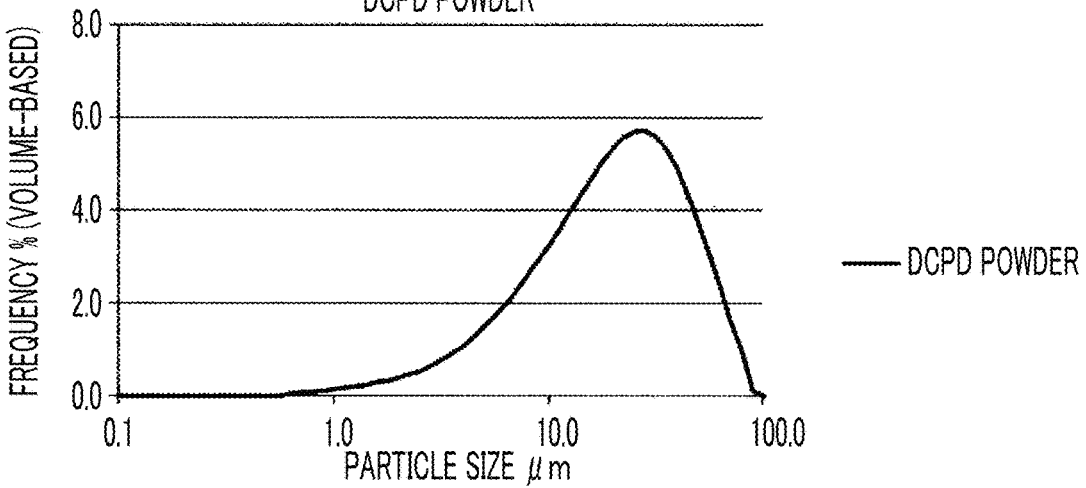
FIG. 16 shows the results of measuring a particle size distribution of a DCPD powder.

The measurement results for the mixed powder are shown in FIG. 14, the measurement results for the TTCP powder are shown in FIG. 15, and the measurement results for the DCPD powder are shown in FIG. 16.

Regarding the powder, in a case in which the particle size (μm) at the point of cumulative 10% from the finer size side is denoted as d10; the particle size (μm) at the point of cumulative 25% from the finer size side is denoted as d25; the particle size (μm) at the point of cumulative 50% from the finer size side is denoted as d50; the particle size (μm) at the point of cumulative 75% from the finer size side is denoted as d75; and the particle size (μm) at the point of cumulative 90% from the finer size side is denoted as d90, TTCP had a value of d50=7.4 μm, which corresponds to the median diameter, and DCPD has a value of d50=19.5 μm. TTCP and DCPD are mixed such that the final ratio of the numbers of atoms of Ca/P will be 1.5, and more specifically, TTCP and DCPD are mixed at a molar ratio of TTCP:DCPD=1:2, or at a ratio of TTCP:DCPD=219.8 g:206.5 g. This mixture is referred to as Ca phosphate powder.

The calcium phosphate powder thus mixed has a value of d50=17.0 μm, and includes particles having a particle size of 5 to 15 μm at a proportion of about 35% by volume and particles having a particle size of 25 to 100 μm at a proportion of 32% by volume.

TABLE 5

|  | d10 μm | d25 μm | d50 μm | d75 μm | d90 μm |
|---|---|---|---|---|---|
| Mixed powder | 4.7 | 8.8 | 17.0 | 29.5 | 43.3 |
| TTCP powder | 1.5 | 4.5 | 7.4 | 11.3 | 16.0 |
| DCPD powder | 5.3 | 10.3 | 19.5 | 32.6 | 47.1 |

Example 9

Fluidity Test for Calcium Phosphate Powder

Regarding powders, TTCP having an average particle size of 7 μm, DCPD having an average particle size of 60 μm, and a mixture of TTCP and DCPD (mixed such that the ratio of the numbers of atoms of Ca/P would be 1.5) were prepared. Regarding the mixture of TTCP and DCPD, more specifically, TTCP and DCPD were mixed at a molar ratio of TTCP:DCPD=1:2, or at a ratio of TTCP:DCPD=219.8 g:206.5 g.

Fluidity (flow function) of the powders described above was measured by the following method. As the measuring apparatus, "Powder Flow Tester, PFT" manufactured by Ametek Brookfield, Inc. was used, and the flow function measured by selecting the standard flow function is a value represented by the formula: σ1/fc, wherein fc represents the breaking strength, and σ1 represents the maximum principal stress. The flow function value was evaluated according to the following criteria.

TABLE 6

| Flow function value | Criteria for fluidity | Evaluation rank |
|---|---|---|
| 10 or greater | Flows extremely easily | 5 |
| 4 to less than 10 | Flows easily | 4 |
| 2 to less than 4 | Being adhesive, slightly difficult to flow | 3 |
| 1 to less than 2 | Being highly adhesive, difficult to flow | 2 |
| 0 to less than 1 | Does not flow | 1 |

The flow function values and the evaluation results are shown in the following table. Despite that the TTCP and DCPD thus mixed do not undergo large changes in the weight and volume, it seemed that the flow function value was not greatly affected by TTCP, and the flow function value was not a value intermediate between TTCP and DCPD, but a value close to that of DCPD.

TABLE 7

|  | Flow function value | Evaluation rank |
|---|---|---|
| TTCP | 3.34 | 3 |
| DCPD | 5.13 | 4 |
| Mixed powder | 4.87 | 4 |

As shown by the flow function value, TTCP has poor fluidity, and in a case in which a powder is recoated with TTCP only, TTCP adheres to the roller, or concavities and convexities having a size of several millimeters or more, which are visible by naked eyes, are formed on the surface layer face of the TTCP powder that should be originally flat. In a case in which DCPD is mixed with TTCP, the mixed powder does not adhere to the roller, and the powder can be recoated without having concavities and convexities on the surface layer face of the mixed powder.

A TTCP powder is highly reactive to an organic acid solution, and from the viewpoint of reactivity, the TTCP powder is adequate for shaping with a 3D powder lamination printer. However, the fluidity is such that the flow function is less than 4.0, and defective recoating occurs.

Generally, fluidity is related to the particle size, and a smaller particle size leads to poor fluidity. As the particle size is smaller, the specific surface area increases, and the influence of the surface becomes noticeable compared to the influence of the volume that is proportional to the mass. The influence of attractive force that draws particles together, such as van der Waals force or electrostatic force, which works on the surface of a certain powder particle and the surface of a neighboring powder particle, becomes highly noticeable.

TTCP is such that the d50 value, which can be regarded as a representative size of the particle size, is φ7.4 μm, and this is smaller than the d50=φ19.5 μm of DCPD. Even the value of d90, which lies on the large size side of the particle size distribution, is 16.0 μm, which is smaller than d90=47.1 μm of DCPD, and TTCP is not mixed with large particles.

In a case in which TTCP and DCPD are mixed at a predetermined molar ratio, the d50 value becomes 17.0 μm, and even if the mixed powder includes particles having a particle size of 5 to 15 μm at a proportion of about 35% by volume, the influence of including particles having a particle size of 25 to 100 μm at a proportion of 32% is exerted. Regarding the fluidity, while the flow function value is 3.34 in the case of TTCP only, the flow function value is 4.87 in the case of the mixed powder, and the flow function value becomes close to 5.13 in the case of DCPD only. Thereby, defective recoating does not occur, and 3D powder lamination printing is enabled.

Example 10

Rat Test

An evaluation test for bone regeneration was carried out using a calcium phosphate molded article coated with CBE3 (recombinant gelatin comprising an amino acid sequence of SEQ ID NO:1).

The calcium phosphate molded article was produced as follows.

<Method for Producing Calcium Phosphate Molded Article>

Regarding an ink, an aqueous solution of sodium citrate adjusted to pH 3.15 was produced by mixing 1.2 mol/L citric acid and 1.2 mol/L trisodium citrate dihydrate at a volume ratio of citric acid:trisodium citrate dihydrate=3:1. This aqueous solution of sodium citrate thus produced was referred to as Na citrate ink.

Regarding a powder, in a case in which the particle size (μm) at the point of cumulative 10% from the finer size side is denoted as d10; the particle size (μm) at the point of cumulative 25% from the finer size side is denoted as d25; the particle size (μm) at the point of cumulative 50% from the finer size side is denoted as d50; the particle size (μm) at the point of cumulative 75% from the finer size side is denoted as d75; and the particle size (μm) at the point of cumulative 90% from the finer size side is denoted as d90, a TTCP powder having a d50 of 7.4 μm, which corresponds to the median diameter, and a DCPD powder having a d50 of 19.5 μm were prepared, and the two powders were mixed such that the final ratio of the numbers of atoms of Ca/P would be 1.5. More specifically, the powders were mixed at a molar ratio of TTCP:DCPD=1:2, or at a ratio of TTCP:DCPD=219.8 g:206.5 g. This mixture was referred to as Ca phosphate powder.

The Ca phosphate powder thus mixed includes particles having a particle size of 5 to 15 μm at a proportion of about 35% by volume and particles having a particle size of 25 to 100 μm at a proportion of 32% by volume.

A 3D printer (Z-Printer 310 Plus) was used, the ink and the powder were replaced with the Na citrate ink and the Ca phosphate powder, and the lamination thickness was set to 100 μm.

Figure 17:
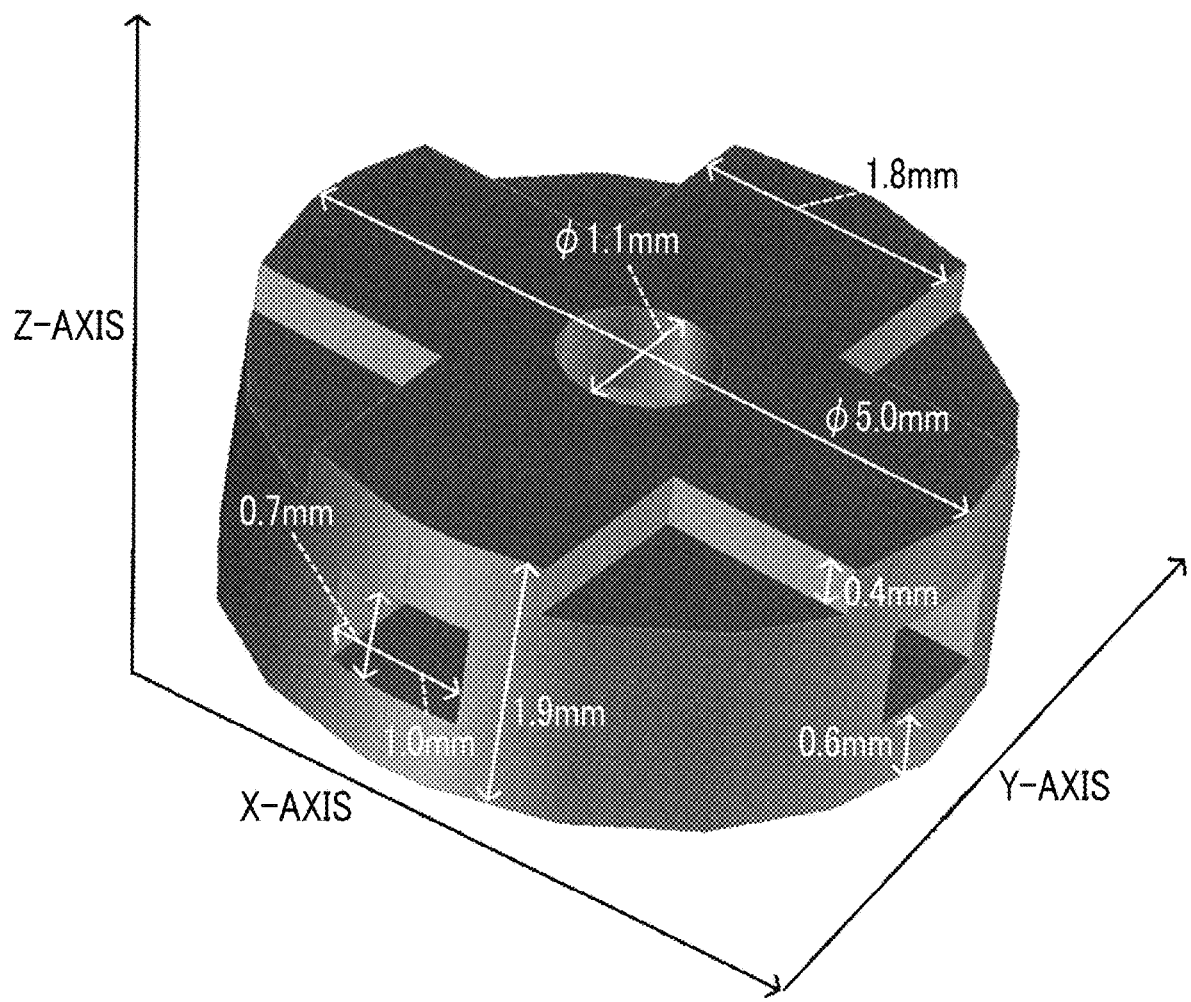
FIG. 17 shows a schematic diagram of a calcium phosphate molded article used in a rat test.

After a molded article was molded with the 3D printer, the molded article was dried inside the 3D printer at 35° C. for one hour, and any excess powder was removed using compressed air (an air blow stream producing compressed air adjusted to 0.15 MPa using an air gun). This molded article was heated in a muffle furnace by increasing the temperature by 100° C. in one hour each time, and then, the molded article was sintered for 2 hours at 1,100° C. Heating for sintering was turned off, and the molded article was left to stand therein for 8 hours without opening the lid of the muffle furnace. After the muffle furnace reached a temperature lower than or equal to 100° C., the sintered molded article was taken out, and thus a molded article was obtained. A schematic diagram of the calcium phosphate molded article is shown in FIG. 17.

The structure is a disc-shaped structure having a diameter of (I) 5 mm and a height of 1.9 mm.

A communicating hole having a size of 0.7×1.0 mm is formed in a cross shape in the X-direction and the Y-direction, parallel to the bottom face of the disc at an intermediate height of the disc.

A communicating hole of ϕ1.1 mm is formed in the Z-axis direction so as to penetrate through the center of the cross shape.

On the top face side of the disc, a convexity having a width of 1.8 mm and a height of 0.4 mm is formed in the X-direction and the Y-direction on the upper side of the communicating hole.

The molded article was coated with CBE3. The method for producing an aqueous solution of CBE3 and coating of Ca phosphate with CBE3 were as follows.

7 mass % of CBE3 was dissolved in an aqueous solution for injection manufactured by Hikari Pharmaceutical Co., Ltd., the solution was heated for 30 minutes in an oven at 45° C. to dissolve the solution, and thus an aqueous solution of CBE3 was produced.

The calcium phosphate molded article was immersed in the aqueous solution of CBE3, the calcium phosphate molded article was subjected to a vacuum degassing treatment in a desiccator from atmospheric pressure to −0.09 MPa, and the molded article was left to stand for 10 minutes while air dissolved in the aqueous solution or air from the voids inside the Ca phosphate molded article was removed. The pressure was returned to the atmospheric state, similar operations were carried out two times, and then the calcium phosphate molded article was taken out. Any excess aqueous solution of CBE3 adhering to the Ca phosphate molded article was removed, and the molded article was dried in an oven at 50° C. for 3 hours.

Thermal crosslinking of CBE3 was carried out as follows. In an oven capable of nitrogen purging by vacuum drawing, nitrogen purging was repeated several times by vacuum drawing to reach about 2 hPa, and then heating was performed for about 4 hours at 150° C. in a nitrogen atmosphere at 1013 hPa.

The periosteum was detached from the parietal bone of a rat, subsequently a defect with a diameter of 5 mm was provided in the parietal bone, and a test material was installed therein. Subsequently, the detached periosteum was attached, and then the skin was sutured.

(Production of Pathologic Specimen)

After completion of the test period, the rat was brought to death by exsanguinations, and the head portion was collected from the rat. From a specimen obtained after removing soft tissues such as eyeballs and brain, the enthesis part was trimmed and embedded in a resin. Slices having a thickness of 5 μm were cut out from the same embedded specimen using a microtome, and the slices were subjected to haematoxylin & eosin staining (H & E) and von Kossa staining.

(Micro CT Analysis)

Figure 18:
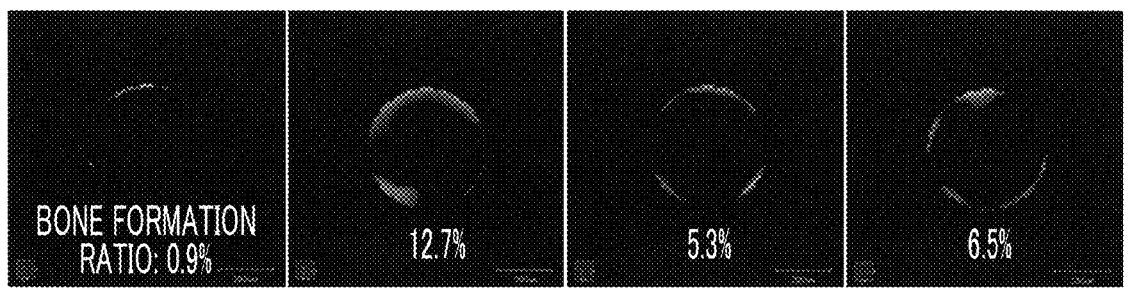
FIG. 18 shows the results of a microfocus CT analysis in Test A (control: defect only).

For Test A (control: defect only), a microfocus CT analysis was performed. Microfocus CT is R-mCT manufactured by Rigaku Corporation, the tube voltage is 90 kV, the tube current is 100 μA, the distance of X-ray focus—detector (FDD) is 292 mm, and the distance of X-ray focus—center of rotation (FOD) is 73 mm. The analysis results of microfocus CT are shown in FIG. 18. In regard to the microfocus CT analysis, in the control (defect only), bone regeneration from the outer periphery of existing bones can be seen; however, regeneration filling in the defect in the rat head portion cannot be seen.

Figures 19, 20:
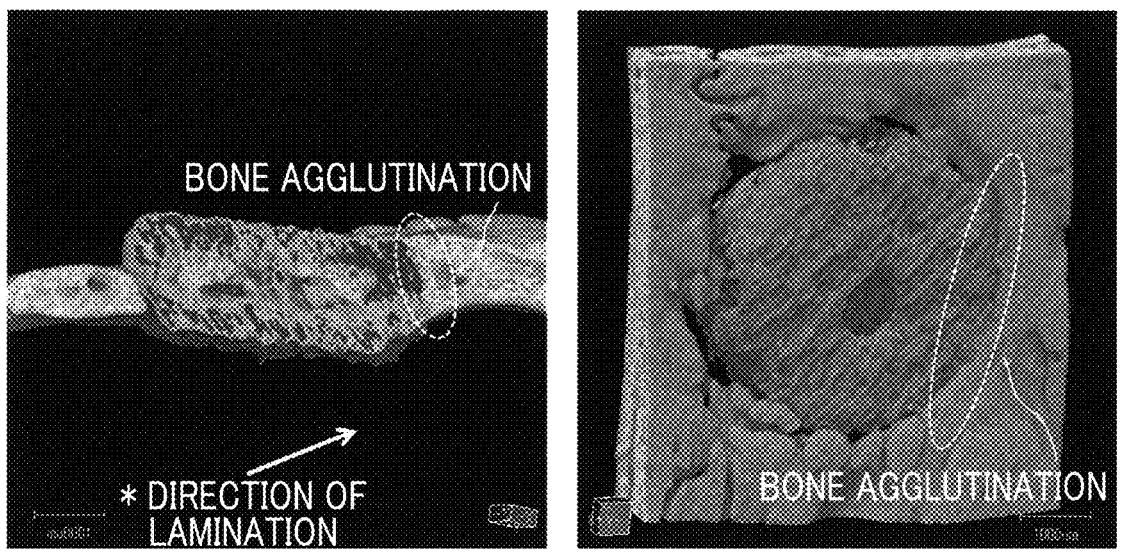
FIG. 19 shows the result of a micro CT analysis obtained for eight weeks after transplantation of molded article B into a rat.
FIG. 20 shows the results of a micro CT analysis obtained in every two weeks from week 0 (zero) for the transplanted molded article B.

The results of a micro CT analysis for eight weeks after transplantation of Test B (Ca phosphate molded article coated with CBE3 (molded article B)) into a rat are shown in FIG. 19. Sufficient bone agglutination at the site where the molded article B and the rat autologous bone were in contact can be recognized. The external appearance shape of the molded article B, and the internal structure formed by a 3D printer both maintain the shapes.

The results of a micro CT analysis of the transplanted molded article B for every two weeks from week zero (0) are shown in FIG. 20. After four weeks, bone was newly generated in the cross-shaped communicating hole having a size of about 0.7×1.0 mm produced as designed, and the state of growing could be confirmed after six weeks.

Figure 21:
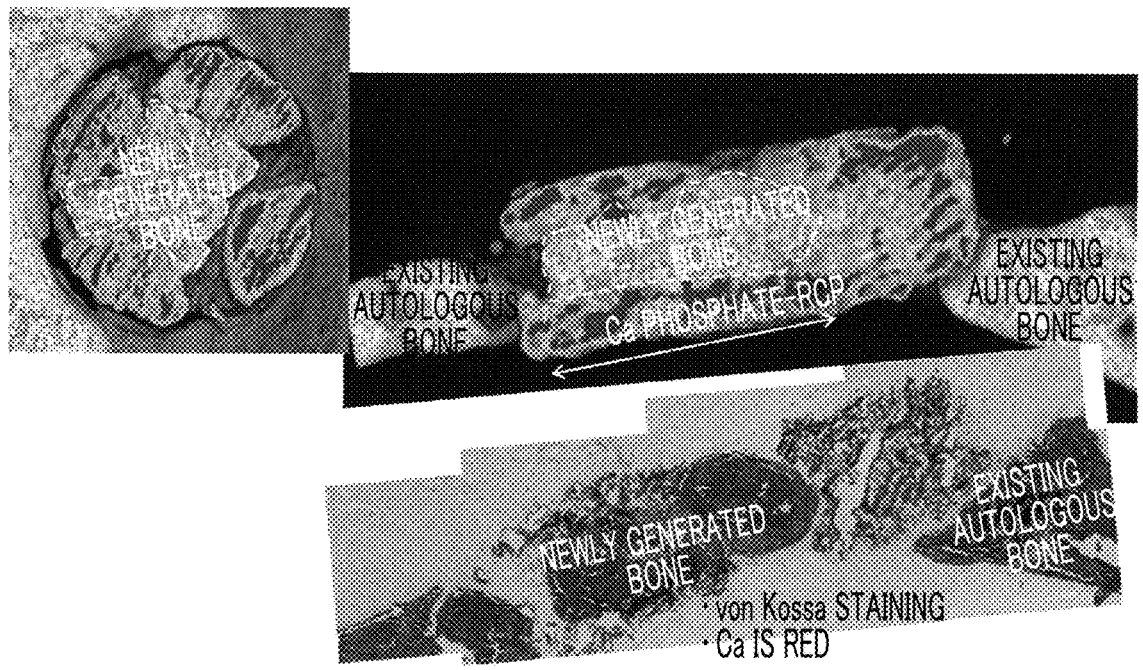
FIG. 21 shows the results of a micro CT analysis of the transplanted molded article B after eight weeks.

The micro CT analysis results of the transplanted molded article B after eight weeks are shown in FIG. 21. The analysis conditions are similar to the conditions for Test A described above. Bone was newly generated in the communication hole having a size of about 0.7×1.0 mm thus produced as designed, and bone grew up to 3.5 mm at a long part. It can also be confirmed by pathologic specimen and von Kossa staining that the matter filling the interior of the communicating hole is certainly bone.

Figure 22:
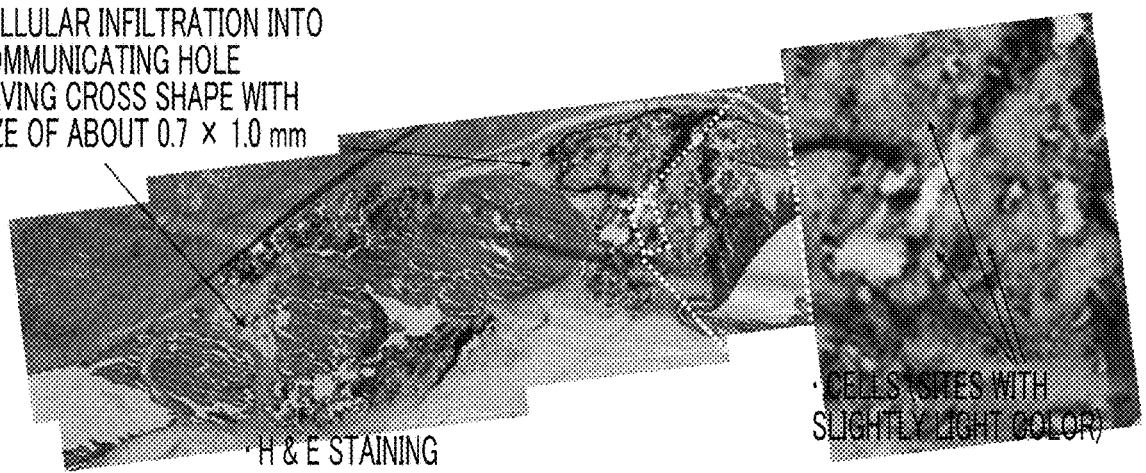
FIG. 22 shows a pathologic specimen and the results of H & E staining for the transplanted molded article B obtained after eight weeks.

The pathologic specimen of the transplanted molded article B after eight weeks and the results of H & E staining are shown in FIG. 22. The pathologic specimen of FIG. 22 is close to the pathologic specimen of FIG. 21. It is understood that in the vicinity of the site where bone was newly generated inside the cross-shaped communicating hole having a size of 0.7×1.0 mm produced as designed by 3D printing, cells infiltrated and formed soft tissue. At the time of 3D printing powder lamination, cells infiltrated even into the sparse layers (about 20 to 80 μm) of the sparse-compact lamination structure autonomously formed, and the cells formed soft tissue.

Figure 23:
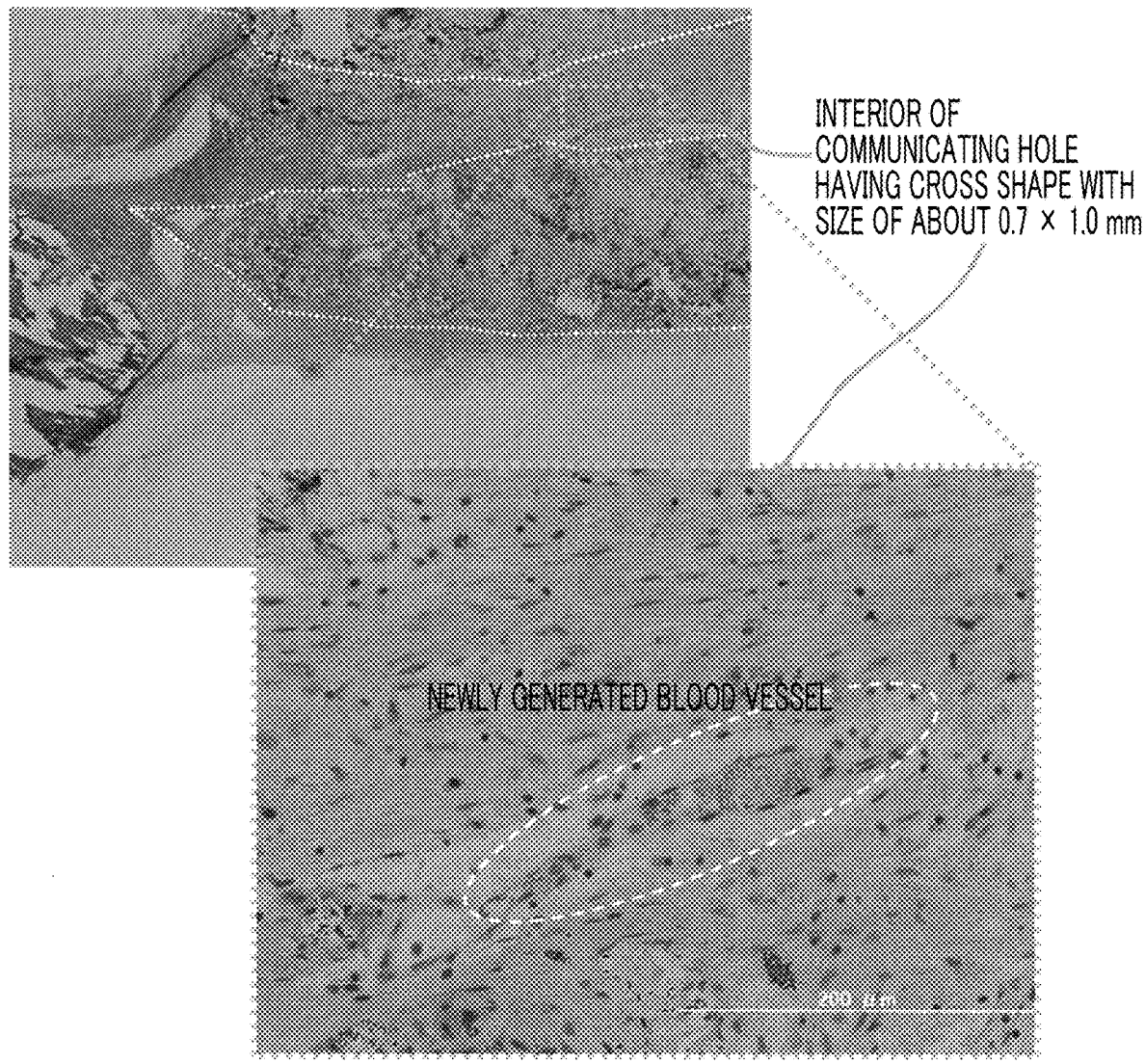
FIG. 23 shows a pathologic specimen and the results of H & E staining for the transplanted molded article B obtained in a rat (second rat) after eight weeks.
Figure 24:
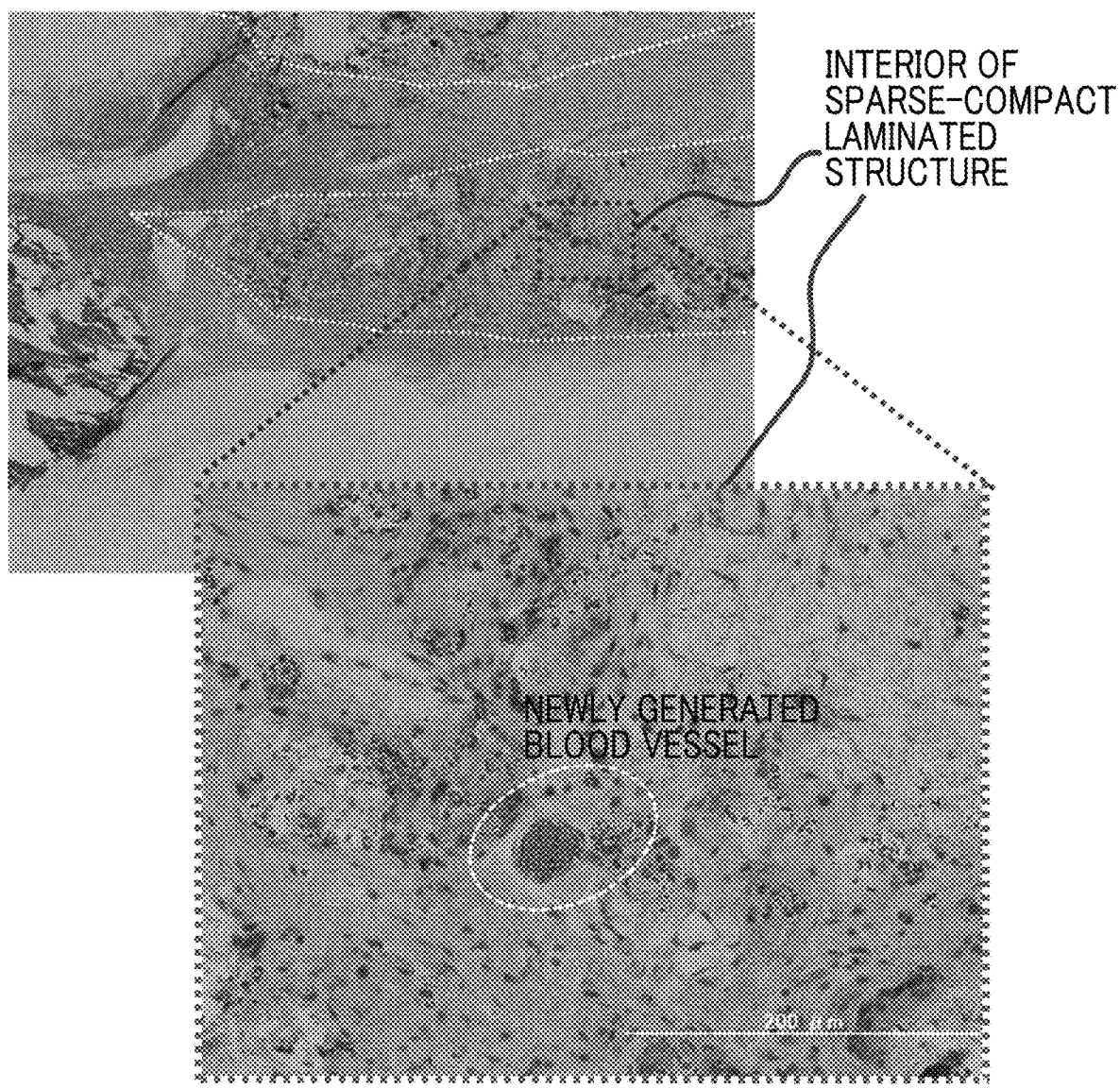
FIG. 24 shows a pathologic specimen and the results of H & E staining for the transplanted molded article B obtained in a rat (second rat) after eight weeks.

In regard to the transplanted molded article B, the pathologic specimen after eight weeks of another rat (second animal) different from the above-described one, and the results of H & E staining are shown in FIG. 23 and FIG. 24. New generation of blood vessels inside a communicating hole having a size of 0.7×1.0 mm produced as designed by 3D printing was confirmed. New generation of blood vessels in the sparse layers (about 20 to 80 μm) of the sparse-compact laminated structure autonomously formed at the time of 3D powder lamination printing was also confirmed.

Figure 25:
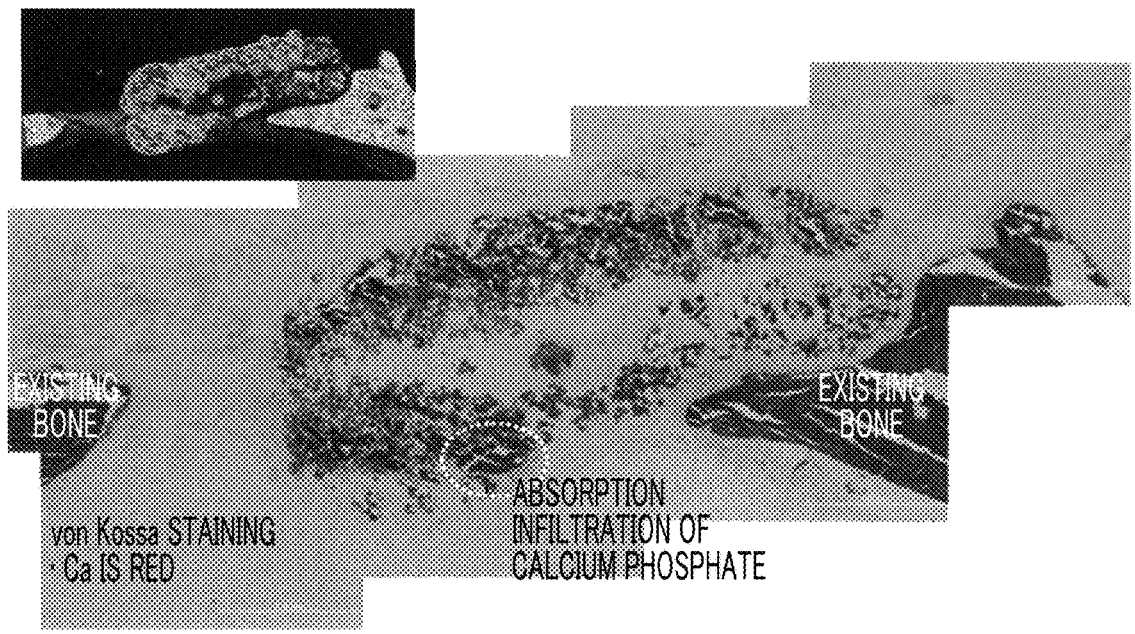
FIG. 25 shows a pathologic specimen and the results of von Kossa staining for the transplanted molded article B obtained in a rat (third rat) after eight weeks.

For the transplanted molded article B, the pathologic specimen after eight weeks of another rat (third animal) different from those described above and the results of von Kossa staining are shown in FIG. 25. It can be confirmed that calcium phosphate has been absorbed and replaced to be substituted by bone.

Example 11

Effect of Concentration of Organic Acid Solution

<Method for Producing Calcium Phosphate Molded Article>

A 1.0 mol/L aqueous solution of sodium citrate adjusted to pH 3.15 was produced by mixing 1.0 mol/L citric acid and 1.0 mol/L trisodium citrate dihydrate at a volume ratio of citric acid:trisodium citrate dihydrate=3:1.

A 1.2 mol/L aqueous solution of sodium citrate adjusted to pH 3.15 was produced by mixing 1.2 mol/L citric acid and 1.2 mol/L trisodium citrate dihydrate at a volume ratio of citric acid:trisodium citrate dihydrate=3:1.

Regarding a powder, in a case in which the particle size (μm) at the point of cumulative 10% from the finer size side is denoted as d10; the particle size (μm) at the point of cumulative 25% from the finer size side is denoted as d25; the particle size (μm) at the point of cumulative 50% from the finer size side is denoted as d50; the particle size (μm) at the point of cumulative 75% from the finer size side is denoted as d75; and the particle size (μm) at the point of cumulative 90% from the finer size side is denoted as d90, a TTCP powder having a d50 of 7.4 μm, which corresponds to the median diameter, and a DCPD powder having a d50 of 19.5 μm were prepared, and the two powders were mixed such that the final ratio of the numbers of atoms of Ca/P would be 1.5. More specifically, the powders were mixed at a molar ratio of TTCP:DCPD=1:2, or at a ratio of TTCP:DCPD=219.8 g:206.5 g. This mixture was referred to as Ca phosphate powder.

The Ca phosphate powder thus mixed includes particles having a particle size of 5 to 15 μm at a proportion of about 35% by volume and particles having a particle size of 25 to 100 μm at a proportion of 32% by volume. The particle size was measured using LMS-2000e manufactured by Seishin Enterprise Co., Ltd. as a laser diffraction type particle size distribution analyzer, and using ethanol as the dispersing medium.

The 1.0 mol/L aqueous solution of sodium citrate or the 1.2 mol/L aqueous solution of sodium citrate was dropped by jetting onto the Ca phosphate powder described above.

In regard to the coating amount of the organic acid solution, the calcium phosphate powder is removed from the 3D printer, a plastic container for which the weight has been measured in advance is placed at the site where a calcium phosphate molded article is originally formed, the organic acid solution is jetted out onto the plastic container as if a three-dimensional article designed to have a volume of 1 cm$^3$ is shaped. The weight of the plastic container is measured in a state of containing the organic acid solution, and thus the weight of the jetted organic acid solution is measured. The weight of the organic acid solution required for shaping the three-dimensional article designed to have a volume of 1 cm$^3$ is designated as the coating amount of the organic acid solution and is expressed in the unit of g/1 cm$^3$.

The 1.0 mol/L aqueous solution of sodium citrate was tested in the range of 0.12 g/1 cm$^3$ to 0.38 g/1 cm$^3$, and the 1.2 mol/L aqueous solution of sodium citrate was tested in the range of 0.215 g/1 cm$^3$ to 0.29 g/1 cm$^3$.

The powder and the aqueous solutions of sodium citrate were introduced into Z-Printer 310 Plus (3D Systems Corporation (formerly known as Z Corporation)), and cuboids having a size of 20×20×8 mm were produced.

A 3D printer (Z-Printer 310 Plus) was used, the ink and the powder were replaced with the Na citrate ink and the Ca phosphate powder, and the lamination thickness was set to 100 μm.

After the molded article was molded with the 3D printer, the molded article was dried inside the 3D printer at 35° C. for one hour, and any excess powder was removed using compressed air (an air blow stream producing compressed air adjusted to 0.15 MPa using an air gun). This molded article was heated in a muffle furnace by increasing the temperature by 100° C. in one hour each time, and then, the molded article was sintered for 2 hours at 1,100° C. Heating for sintering was turned off, and the molded article was left to stand therein for 8 hours without opening the lid of the muffle furnace. After the muffle furnace reached a temperature lower than or equal to 100° C., the sintered molded article was taken out, and thus the molded article was obtained. The molded article underwent about 10% shrinkage in the respective directions after sintering, and thus the size became about 18×18×7.2 mm.

For the calcium phosphate molded articles thus produced, measurement of the compressive strength and the state of warping of the bottom face were carried out.

The measurement of the compressive strength was carried out using a digital force gauge, ZTA-1000N, manufactured by Imada, Inc., which is the same as the vertical type electric measurement stand, MX2, manufactured by Imada, Inc. Load was exerted on a sample having a size of about 18×18×7.2 mm in the longitudinal direction, at a rate of 0.17 mm/sec, and the shape of the sample was precisely measured with vernier calipers. The compressive strength (MPa) was determined by dividing the maximum load (N) at the time of sample rupture by the cross-sectional area.

Figure 26:
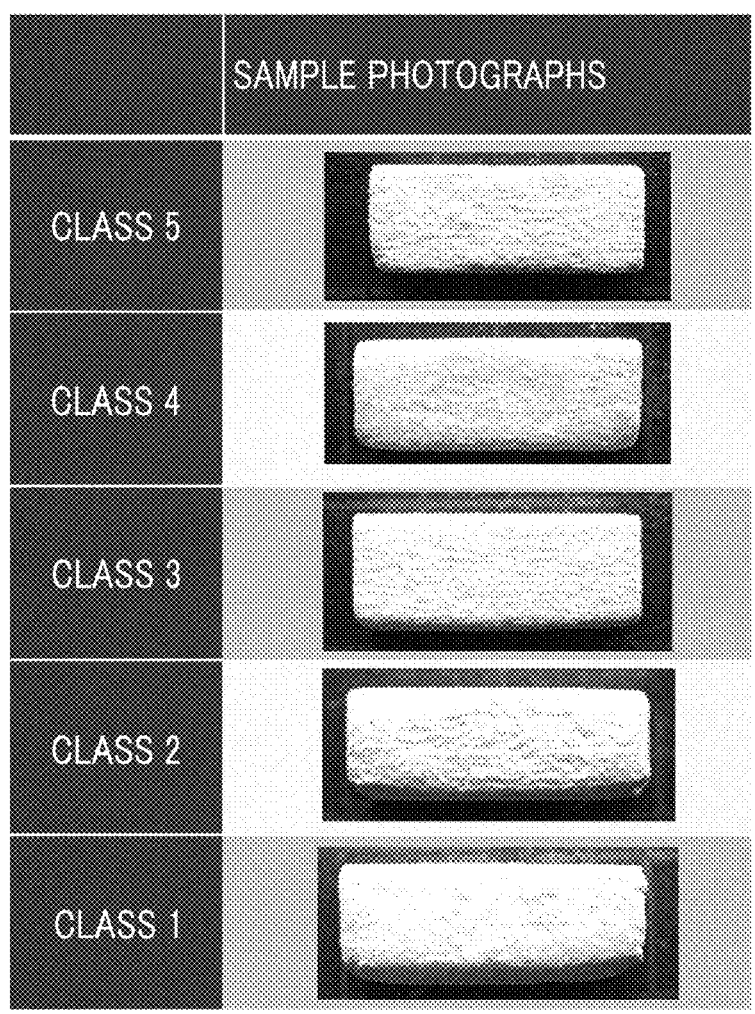
FIG. 26 shows samples of Class 1 to Class 5 in an evaluation for warping of the bottom face.

The evaluation of warping of the bottom face was carried out according the following criteria. Samples of Class 1 to 5 are shown in FIG. 26.

TABLE 8

| | Remarks |
|---|---|
| Class 5 | Seems to have become slightly concave. |
| Class 4 | Warping almost did not occur. |
| Class 3 | Slight warping occurred. |
| Class 2 | Warping occurred significantly. |
| Class 1 | Warping occurred very significantly. Even cracking has occurred in some parts. |

Figure 27:
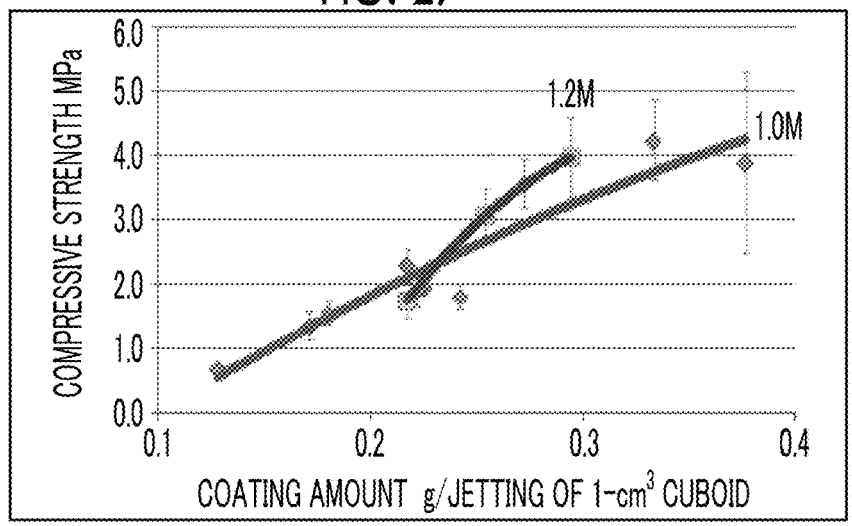
FIG. 27 shows the relation between the coating amount and the compressive strength in a calcium phosphate molded article.
Figure 28:
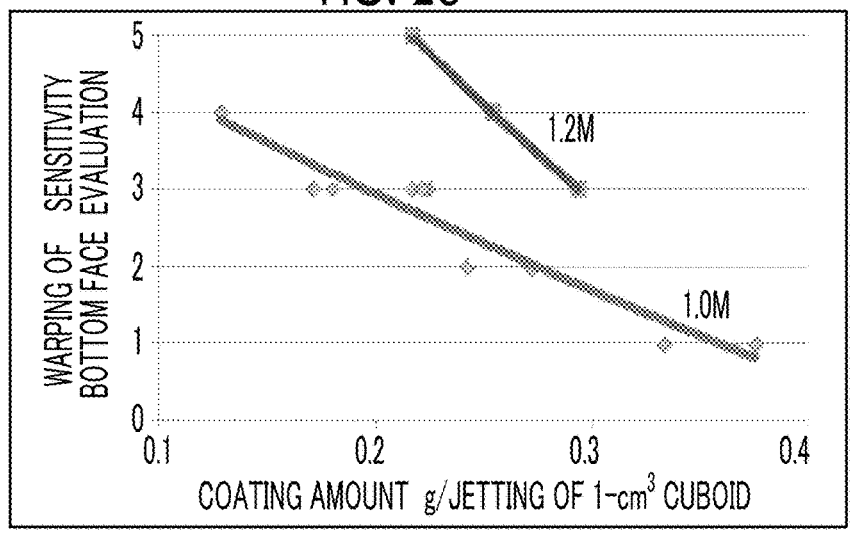
FIG. 28 shows the relation between the coating amount and the warping of the bottom face in a calcium phosphate molded article.
Figure 29:
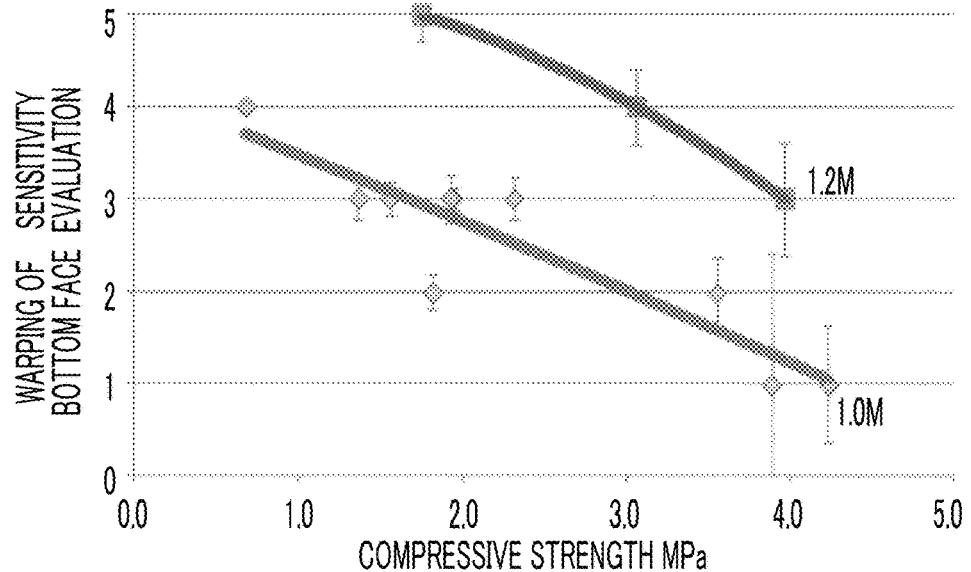
FIG. 29 shows the relation between the compressive strength and the warping of the bottom face in a calcium phosphate molded article.

For a calcium phosphate molded article using the 1.0 mol/L aqueous solution of sodium citrate or the 1.2 mol/L aqueous solution of sodium citrate, the relation between the coating amount and the compressive strength is shown in FIG. 27, the relation between the coating amount and the warping of the bottom face is shown in FIG. 28, and the relation between the compressive strength and the warping of the bottom face is shown in FIG. 29.

From FIG. 27, it is understood that in a case in which the coating amount is increased as a design option, the compressive strength also increases, and the strength as a shaped article is increased. From FIG. 28, it is understood that in a case in which the coating amount is increased as a design option, warping increases, and thereby the shaping precision is lost. FIG. 29 shows the relation between the compressive strength and the warping of the bottom face, which combines the relation between the coating amount and the compressive strength of FIG. 27 and the relation between the coating amount and the warping of the bottom face of FIG. 28. It is clearly understood that the compressive strength and the warping of the bottom face are in a trade-off relationship.

In the results for the 1.0 mol/L aqueous solution of sodium citrate, the compressive strength is 2.0 MPa or higher, and there is no region where the class of the warping of the bottom face is class 4 or higher. However, in the calcium phosphate molded article produced using the 1.2 mol/L aqueous solution of sodium citrate, the compressive strength is 2.0 MPa or higher, and regions where the class of the warping of the bottom face is class 4 or higher are found.

Although the pH values are the same as pH 3.15, in the case of using the 1.2 mol/L aqueous solution of sodium citrate, the trade-off between the compressive strength and the warping of the bottom face is resolved, and more satisfactory results are obtained. That is, high compressive strength and suppression of warping of the bottom face can be achieved simultaneously by using a 1.2 mol/L aqueous solution of sodium citrate.

EXPLANATION OF REFERENCES

11: X-communicating hole of primary hole
12: Y-communicating hole of primary hole
13: Z-communicating hole of primary hole
14: XYZ-communicating hole of primary hole
15, 06: Suture hole
16, 02: Secondary hole
17: Structure reinforcement region
04: Primary hole
21: Calcium phosphate molded article
22: Plastic cylinder
23: Tube
24: Liquid level
25: Syringe

SEQUENCE LISTING

International Patent Application 17F00641 based on the International Patent Cooperation Treaty, Method for producing calcium phosphate molded article JP17020130 20170530

---

What is claimed is:

1. A calcium phosphate molded article formed from calcium phosphate, the molded article having holes communicating with an external space, having a specific gravity of 0.7 g/mL or higher and/or a porosity according to a mercury infusion method of 75% or lower, and having a water absorption infiltration rate of 0.05 mm/second or higher;

the molded article having a structure in which a relatively compact layer and a relatively sparse layer as distinguished by an analysis by nanofocus X-ray CT or microfocus X-ray CT are alternately laminated;

wherein at least five or more layers of the relatively compact layer and at least five or more layers of the relatively sparse layer are alternately laminated; and wherein the calcium phosphate has a ratio of the numbers of atoms of Ca/P of 1.4 to 1.8.

2. The calcium phosphate molded article according to claim 1, wherein in a waveform chart based on a nanofocus X-ray CT image of the calcium phosphate molded article, with a horizontal axis representing a distance in one direction of the molded article and a vertical axis representing a relative CT intensity, peaks and troughs exist alternately.

3. The calcium phosphate molded article according to claim 2, having at least five or more peaks.

4. The calcium phosphate molded article according to claim 2, wherein a pitch between a first peak and a second peak next to the first peak is 50 to 300 μm.

5. A material for transplantation, comprising the calcium phosphate molded article according to claim 1 having a surface partially or entirely coated with a recombinant gelatin.

6. The material for transplantation according to claim 5, wherein the recombinant gelatin is thermally crosslinked or chemically crosslinked.

7. The material for transplantation according to claim 5, wherein the surface of the calcium phosphate molded article coated with recombinant gelatin exists on the surface and in the interior of the material for transplantation.

8. The material for transplantation according to claim 5, wherein the calcium phosphate molded article is block-shaped.

9. The material for transplantation according to claim 5, wherein the calcium phosphate molded article is granular.

* * * * *

SEQUENCE LISTING

```
<160> NUMBER OF SEQ ID NOS: 10

<210> SEQ ID NO 1
<211> LENGTH: 571
<212> TYPE: PRT
<213> ORGANISM: Artificial Sequence
<220> FEATURE:
<223> OTHER INFORMATION: Synthetic: Recombinant

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30
```

-continued

```
Arg Gly Asp Ala Gly Pro Lys Gly Ala Asp Gly Ala Pro
     35                  40                  45
Gly Leu Gln Gly Met Pro Gly Glu Arg Gly Ala Ala Gly Leu Pro Gly
 50                  55                  60
Pro Lys Gly Glu Arg Gly Asp Ala Gly Pro Lys Gly Ala Asp Gly Ala
 65                  70                  75                  80
Pro Gly Lys Asp Gly Val Arg Gly Leu Ala Gly Pro Ile Gly Pro Pro
             85                  90                  95
Gly Glu Arg Gly Ala Ala Gly Leu Pro Gly Pro Lys Gly Glu Arg Gly
            100                 105                 110
Asp Ala Gly Pro Lys Gly Ala Asp Gly Ala Pro Gly Lys Asp Gly Val
            115                 120                 125
Arg Gly Leu Ala Gly Pro Ile Gly Pro Pro Gly Pro Ala Gly Ala Pro
    130                 135                 140
Gly Ala Pro Gly Leu Gln Gly Met Pro Gly Glu Arg Gly Ala Ala Gly
145                 150                 155                 160
Leu Pro Gly Pro Lys Gly Glu Arg Gly Asp Ala Gly Pro Lys Gly Ala
                165                 170                 175
Asp Gly Ala Pro Gly Lys Asp Gly Val Arg Gly Leu Ala Gly Pro Pro
            180                 185                 190
Gly Ala Pro Gly Leu Gln Gly Ala Pro Gly Leu Gln Gly Met Pro Gly
            195                 200                 205
Glu Arg Gly Ala Ala Gly Leu Pro Gly Pro Lys Gly Glu Arg Gly Asp
    210                 215                 220
Ala Gly Pro Lys Gly Ala Asp Gly Ala Pro Gly Ala Pro Gly Leu Gln
225                 230                 235                 240
Gly Met Pro Gly Glu Arg Gly Ala Ala Gly Leu Pro Gly Pro Lys Gly
                245                 250                 255
Glu Arg Gly Asp Ala Gly Pro Lys Gly Ala Asp Gly Ala Pro Gly Lys
            260                 265                 270
Asp Gly Val Arg Gly Leu Ala Gly Pro Ile Gly Pro Pro Gly Glu Arg
            275                 280                 285
Gly Ala Ala Gly Leu Pro Gly Pro Lys Gly Glu Arg Gly Asp Ala Gly
    290                 295                 300
Pro Lys Gly Ala Asp Gly Ala Pro Gly Lys Asp Gly Val Arg Gly Leu
305                 310                 315                 320
Ala Gly Pro Ile Gly Pro Pro Gly Pro Ala Gly Ala Pro Gly Ala Pro
                325                 330                 335
Gly Leu Gln Gly Met Pro Gly Glu Arg Gly Ala Ala Gly Leu Pro Gly
            340                 345                 350
Pro Lys Gly Glu Arg Gly Asp Ala Gly Pro Lys Gly Ala Asp Gly Ala
            355                 360                 365
Pro Gly Lys Asp Gly Val Arg Gly Leu Ala Gly Pro Pro Gly Ala Pro
    370                 375                 380
Gly Leu Gln Gly Ala Pro Gly Leu Gln Gly Met Pro Gly Glu Arg Gly
385                 390                 395                 400
Ala Ala Gly Leu Pro Gly Pro Lys Gly Glu Arg Gly Asp Ala Gly Pro
                405                 410                 415
Lys Gly Ala Asp Gly Ala Pro Gly Ala Pro Gly Leu Gln Gly Met Pro
            420                 425                 430
Gly Glu Arg Gly Ala Ala Gly Leu Pro Gly Lys Gly Glu Arg Gly
            435                 440                 445
Asp Ala Gly Pro Lys Gly Ala Asp Gly Ala Pro Gly Lys Asp Gly Val
```

-continued

```
                450            455             460
Arg Gly Leu Ala Gly Pro Ile Gly Pro Pro Gly Glu Arg Gly Ala Ala
465             470              475             480

Gly Leu Pro Gly Pro Lys Gly Glu Arg Gly Asp Ala Gly Pro Lys Gly
                485             490              495

Ala Asp Gly Ala Pro Gly Lys Asp Gly Val Arg Gly Leu Ala Gly Pro
                500             505             510

Ile Gly Pro Pro Gly Pro Ala Gly Ala Pro Gly Ala Pro Gly Leu Gln
            515             520             525

Gly Met Pro Gly Glu Arg Gly Ala Ala Gly Leu Pro Gly Pro Lys Gly
        530             535             540

Glu Arg Gly Asp Ala Gly Pro Lys Gly Ala Asp Gly Ala Pro Gly Lys
545             550             555             560

Asp Gly Val Arg Gly Leu Ala Gly Pro Pro Gly
            565             570

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 5

Arg Tyr Val Val Leu Pro Arg
1               5
```

```
<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 10

Glu Arg Gly Asp
1
```